US 9,884,266 B2

(12) United States Patent
Dauphas et al.

(10) Patent No.: US 9,884,266 B2
(45) Date of Patent: Feb. 6, 2018

(54) FLUOROPOLYMER PNEUMATICALLY/HYDRAULICALLY ACTUATED LIQUID CHROMATOGRAPHIC SYSTEM FOR USE WITH HARSH REAGENTS

(71) Applicant: ORLAB CHROMATOGRAPHY, LLC, Chicago, IL (US)

(72) Inventors: Nicolas Dauphas, Chicago, IL (US); Francois L. H. Tissot, Chicago, IL (US); Reika Yokochi, Chicago, IL (US); Thomas J. Ireland, Belmont, MA (US); Jingya Hu, Chicago, IL (US)

(73) Assignee: ORLAB CHROMATOGRAPHY, LLC, Chicago, IL (US)

( * ) Notice: Subject to any disclaimer, the term of this patent is extended or adjusted under 35 U.S.C. 154(b) by 607 days.

(21) Appl. No.: 14/326,191

(22) Filed: Jul. 8, 2014

(65) Prior Publication Data

US 2015/0008171 A1    Jan. 8, 2015

Related U.S. Application Data

(60) Provisional application No. 61/843,509, filed on Jul. 8, 2013.

(51) Int. Cl.
*B01D 15/10* (2006.01)
*B01D 15/22* (2006.01)
(Continued)

(52) U.S. Cl.
CPC ....... *B01D 15/1814* (2013.01); *B01D 15/247* (2013.01); *B01D 15/426* (2013.01);
(Continued)

(58) Field of Classification Search
CPC ...... B01D 15/12; B01D 15/14; B01D 15/161; B01D 15/1814; B01D 15/247;
(Continued)

(56) References Cited

U.S. PATENT DOCUMENTS

| | | | | |
|---|---|---|---|---|
| 3,185,211 A | * | 5/1965 | Crawford, Jr. | ......... G01N 30/82 165/71 |
| 3,826,905 A | * | 7/1974 | Valkama | ................ G01N 30/82 127/46.1 |

(Continued)

OTHER PUBLICATIONS

Shimadzu, "Fraction Collector," available at <http://www.shimadzu.com/an/hplc/component/frc.html>, dated May 3, 2012, 1 page.*

(Continued)

*Primary Examiner* — Katherine Zalasky
(74) *Attorney, Agent, or Firm* — Cherskov Flaynik & Gurda, LLC

(57) ABSTRACT

The invention provides a high-performance liquid chromatography system, said system is controlled in temperature by running a fluid in sleeves that surround the different parts of the system. All parts in contact with the fluid are made in fluoropolymer, carbon-filled fluoropolymer, or carbon-fiber fluoropolymer. The system comprises at least one reagent reservoir; at least one mixing chamber, wherein the contents of the at least one reagent reservoir are combined; at least one pump that transfers the contents of the at least one reservoir to the mixing chamber; and at least one modular elution column, wherein the at least one modular elution column contains a temperature control means; a sample injection system connected to an injection loop or 3-way valve to inject the sample solutions in the modular elution columns, at least one manifold or X-Y moving stage to distribute the eluted volumes in different receptacles; at least one return line to automatically reinject selected elution (Continued)

fractions at the top of the column; wherein all moving components of the said system are fluid actuated.

16 Claims, 32 Drawing Sheets

(51) Int. Cl.

| | | |
|---|---|---|
| *B01D 15/18* | (2006.01) | |
| *G01N 30/60* | (2006.01) | |
| *G01N 30/38* | (2006.01) | |
| *G01N 30/44* | (2006.01) | |
| *G01N 30/82* | (2006.01) | |
| *B01D 15/24* | (2006.01) | |
| *B01D 15/42* | (2006.01) | |
| *G01N 30/34* | (2006.01) | |
| G01N 30/04 | (2006.01) | |
| G01N 30/84 | (2006.01) | |
| G01N 30/20 | (2006.01) | |
| G01N 30/88 | (2006.01) | |

(52) U.S. Cl.
CPC ............ *G01N 30/34* (2013.01); *G01N 30/84* (2013.01); *G01N 2030/207* (2013.01); *G01N 2030/347* (2013.01); *G01N 2030/8809* (2013.01)

(58) Field of Classification Search
CPC ........ B01D 15/24; G01N 30/04; G01N 30/06; G01N 30/16; G01N 30/24; G01N 30/38; G01N 30/44; G01N 30/80; G01N 30/82; G01N 30/30; G01N 2030/3007; G01N 2030/3061; G01N 2030/3092; G01N 2030/3084
See application file for complete search history.

(56) References Cited

U.S. PATENT DOCUMENTS

| | | | | |
|---|---|---|---|---|
| 3,966,609 | A * | 6/1976 | Godbille | B01D 15/08 210/198.2 |
| 4,059,994 | A * | 11/1977 | Annino | G01N 30/20 73/23.24 |
| 4,116,046 | A * | 9/1978 | Stein | G01N 30/24 210/198.2 |
| 4,271,703 | A * | 6/1981 | Roof | G01N 30/06 73/863.11 |
| 4,470,910 | A * | 9/1984 | Quemerais | B01D 15/08 210/198.2 |
| 4,534,941 | A * | 8/1985 | Stephens | G01N 30/30 422/109 |
| 4,966,695 | A * | 10/1990 | Joshua | B01D 15/22 165/137 |
| 5,215,556 | A * | 6/1993 | Hiller | G01N 30/30 95/87 |
| 5,248,393 | A * | 9/1993 | Schumacher | B01D 3/32 202/158 |
| 5,670,054 | A * | 9/1997 | Kibbey | B01J 19/0046 210/143 |
| 6,019,897 | A * | 2/2000 | Horsman | B01D 15/14 210/101 |
| 6,139,732 | A * | 10/2000 | Pelletier | B01D 15/14 210/198.2 |
| 6,280,623 | B1 * | 8/2001 | Ma | B01J 47/105 210/264 |
| 6,436,292 | B1 * | 8/2002 | Petro | G01N 30/88 210/143 |
| 7,507,337 | B2 * | 3/2009 | Petro | G01N 30/20 210/101 |
| 2001/0013494 | A1 * | 8/2001 | Maiefski | B01D 15/08 210/656 |
| 2005/0194318 | A1 * | 9/2005 | Ozbal | B01F 5/0085 210/656 |
| 2006/0054544 | A1 * | 3/2006 | Roenneburg | B01D 15/247 210/198.2 |
| 2006/0243666 | A1 * | 11/2006 | Jenkins | B01D 15/12 210/638 |
| 2010/0258485 | A1 * | 10/2010 | Kono | B01D 15/203 210/86 |
| 2010/0276350 | A1 * | 11/2010 | Kono | B01D 15/20 210/198.2 |
| 2010/0281958 | A1 * | 11/2010 | Kono | B01D 15/24 73/61.53 |
| 2011/0146380 | A1 * | 6/2011 | Schleifer | G01N 30/16 73/23.37 |
| 2011/0184658 | A1 * | 7/2011 | Maruyama | G01N 30/82 702/25 |

OTHER PUBLICATIONS

Shimadzu, Brochure, "Prominence preparative HPLC system," available Oct. 10, 2009, 21 pages.*
Agilent Technologies, Brochure, "Agilent GPC Solutions," dated 2009, 29 pages.*
Jablonski et al., Application Note, "Effective use of temperature control in compound isolation," dated 2009, 4 pages.*
Chromtech, "Rheodyne Manual Sample Injector Valves," available at <www.chromtech.com>, accessed Jun. 1, 2017.*
Nge et al. Advances in microfluidic materials, functions, integration and applications. Chem Rev. Apr. 10, 2013; 113(4): 2550-2583.*

* cited by examiner

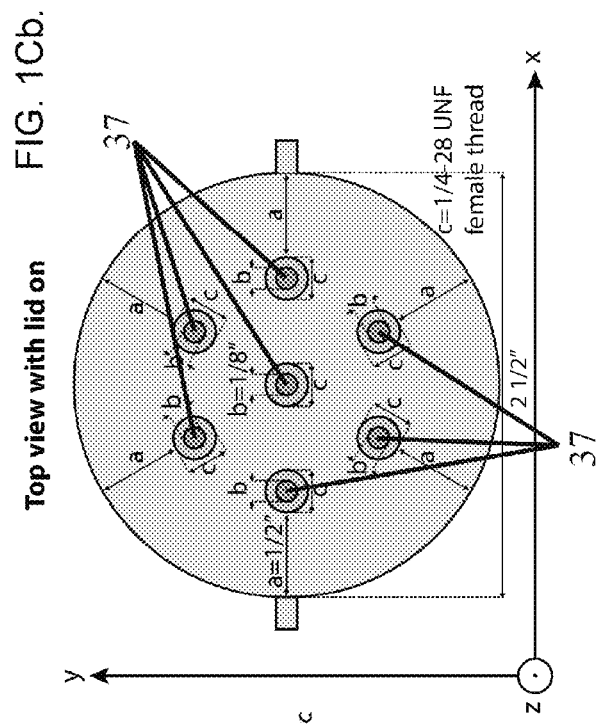
FIG. 1C.
FIG. 1Ca.
FIG. 1Cb.
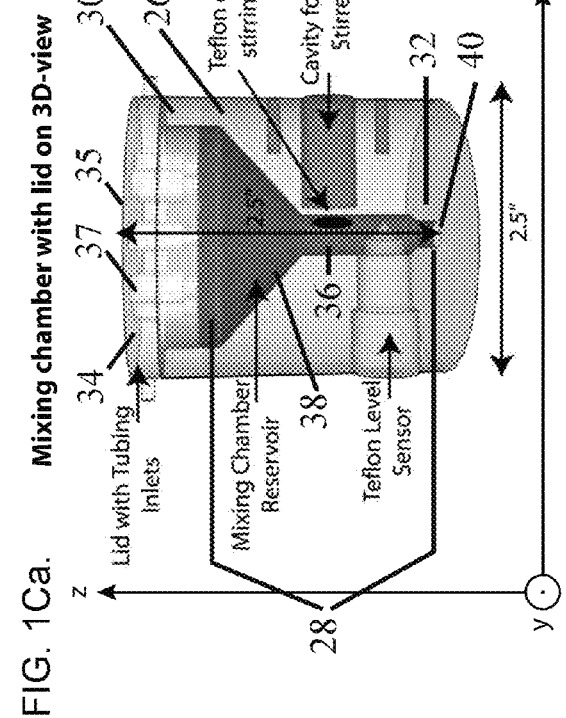
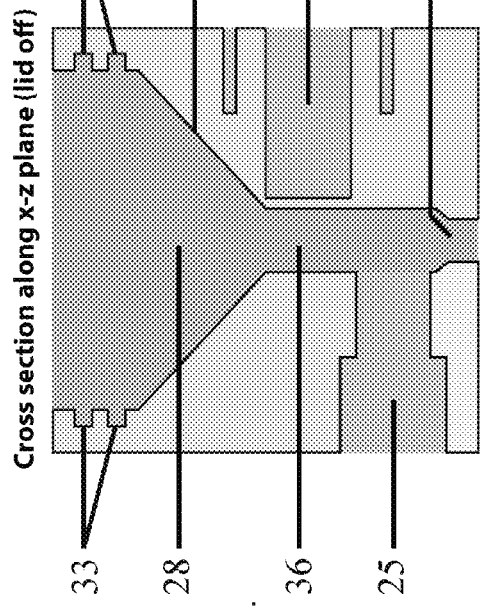
FIG. 1Cc.

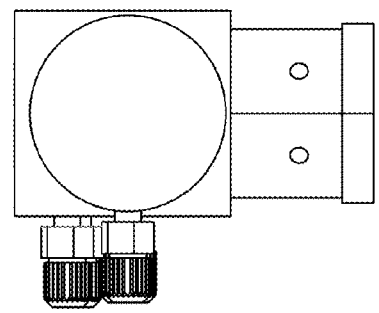
FIG. 1Ef
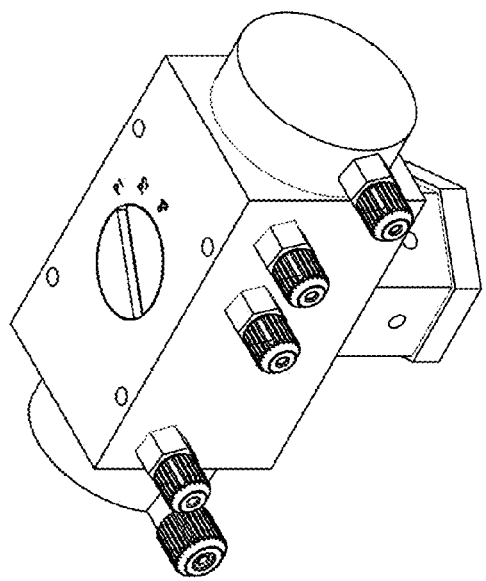
FIG. 1E.
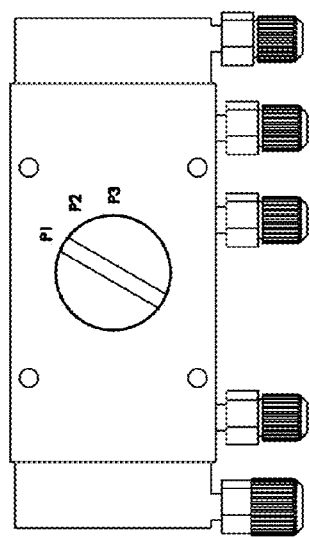
FIG. 1Ea.
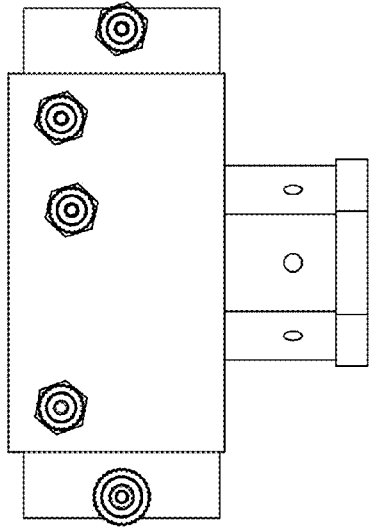
FIG. 1Eb.
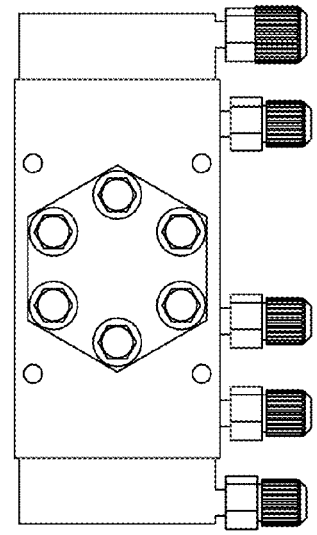
FIG. 1Ec.
FIG. 1Ee

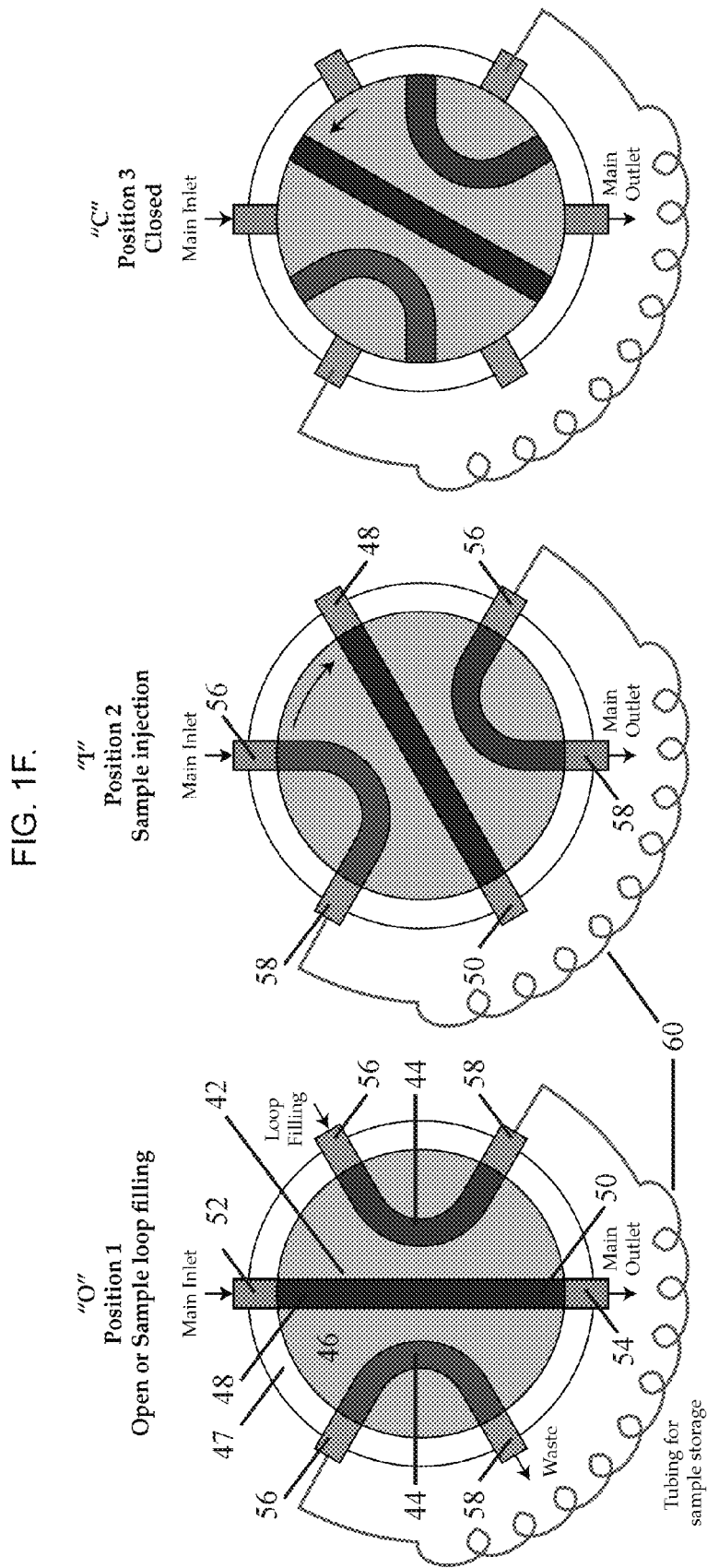

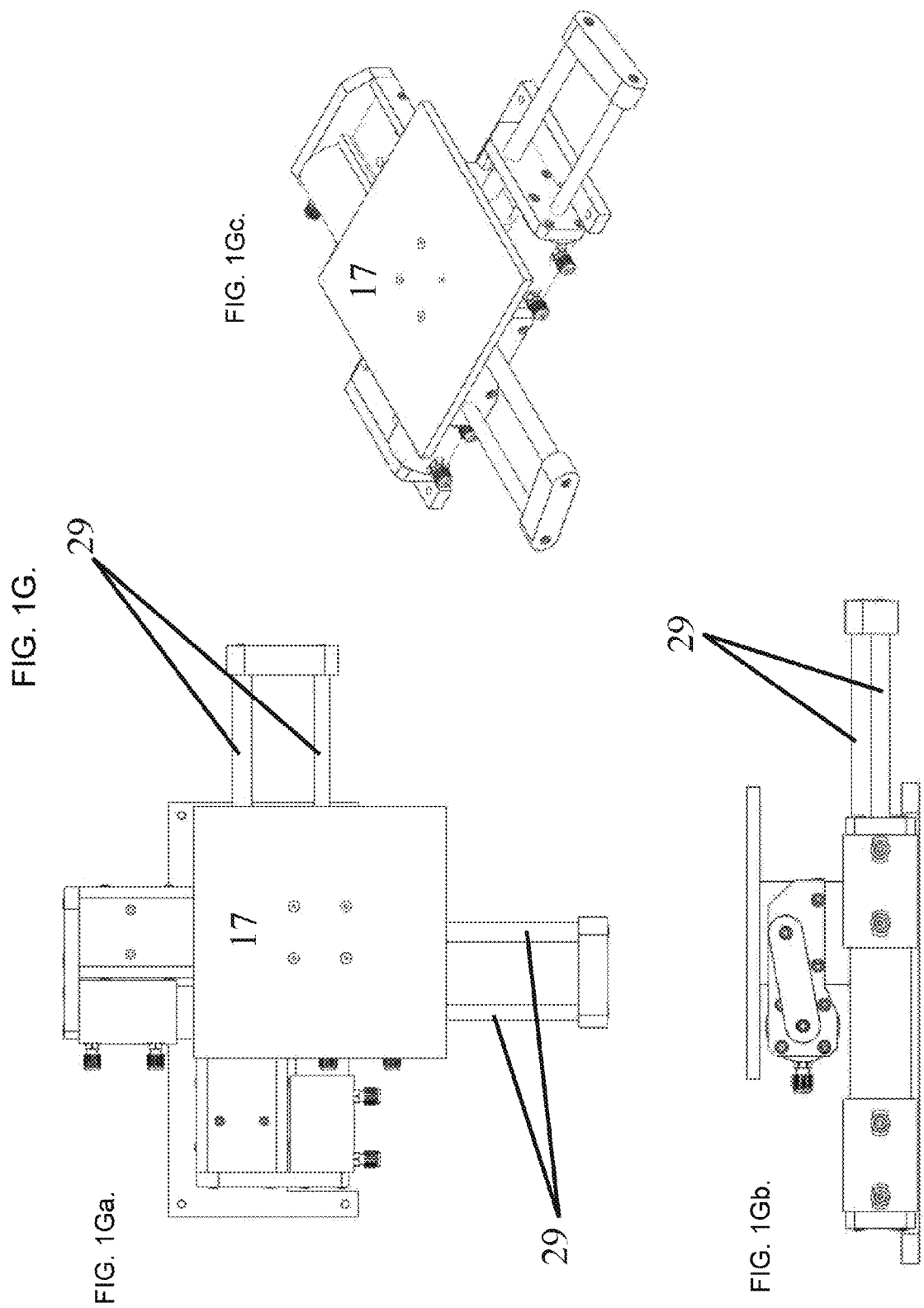

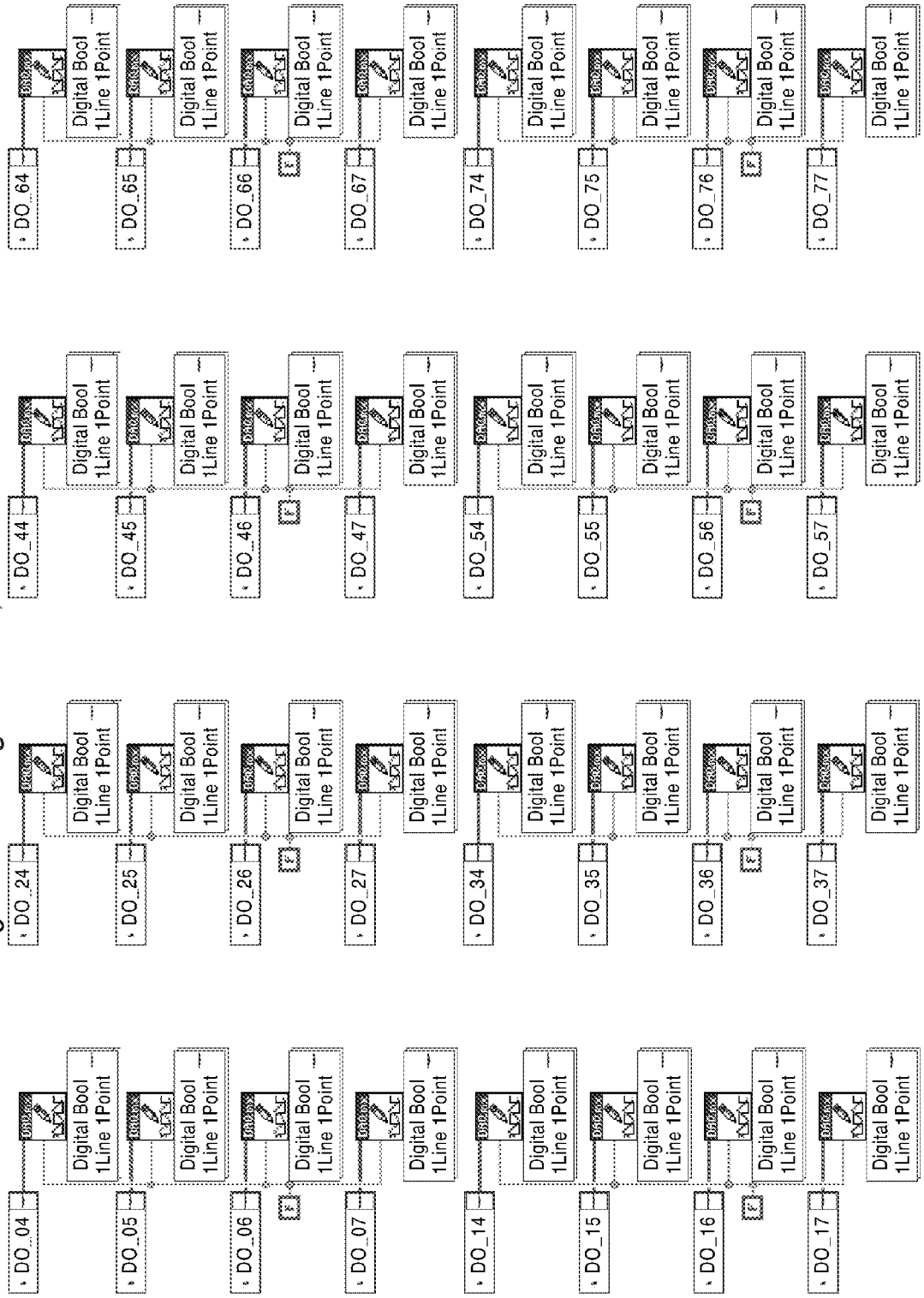

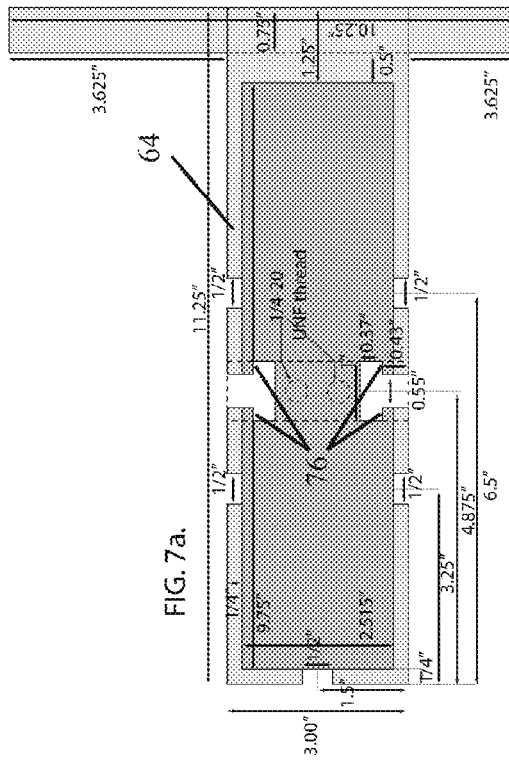
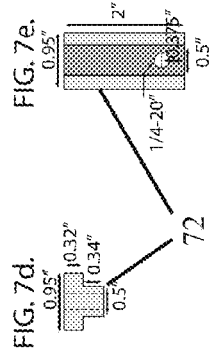
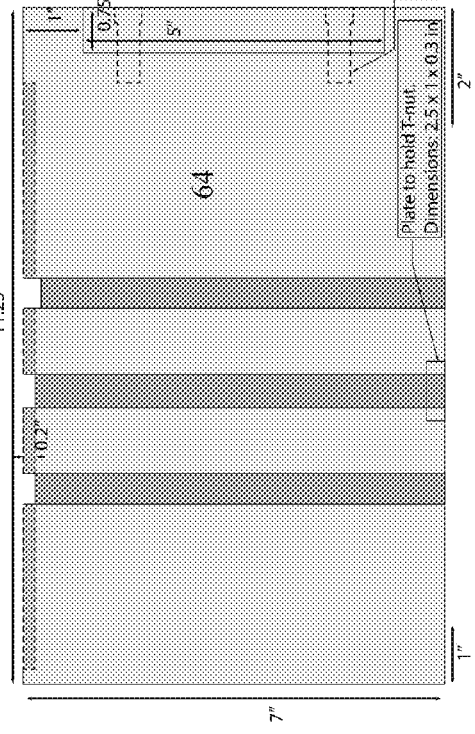
FIG. 7.

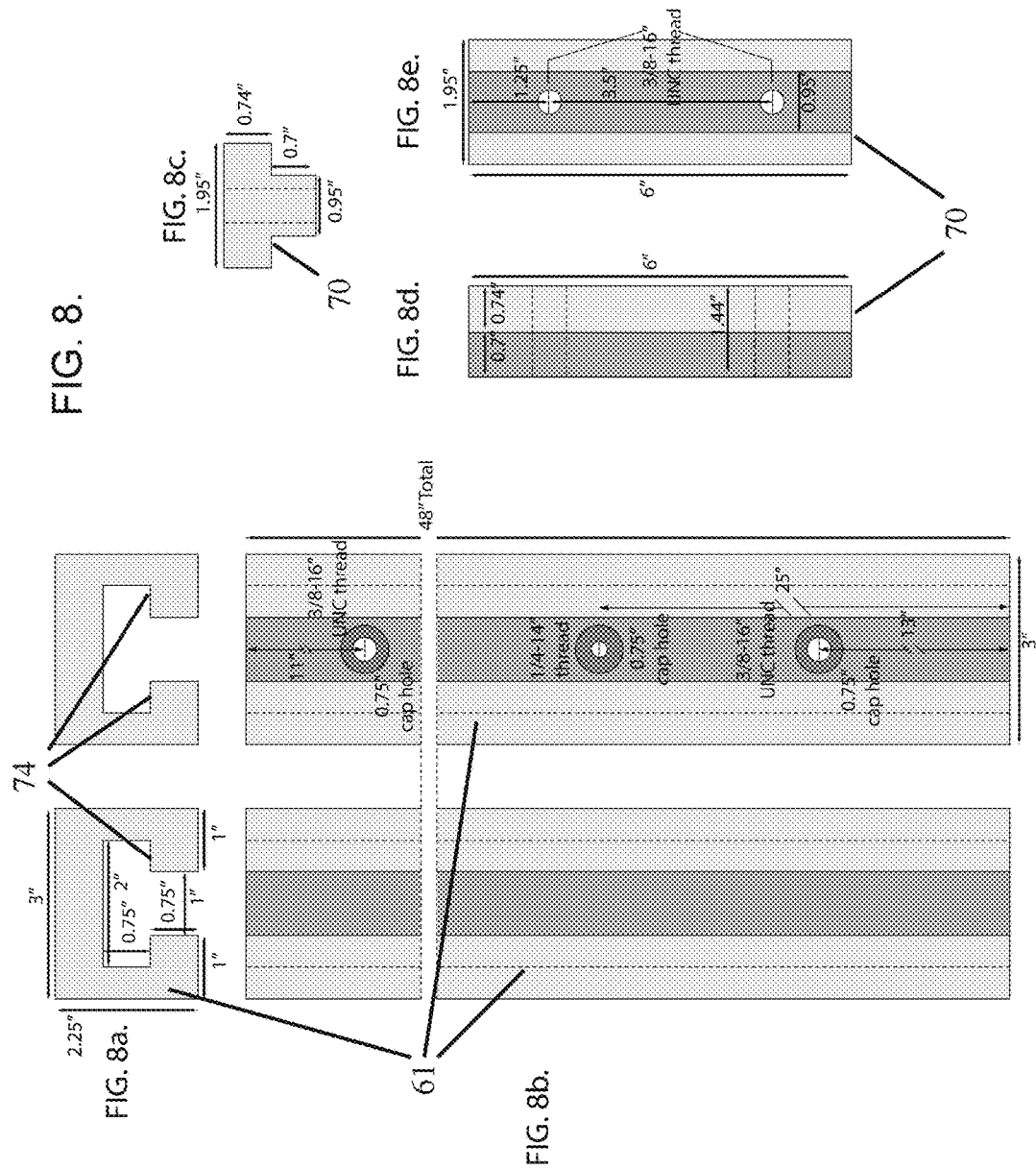

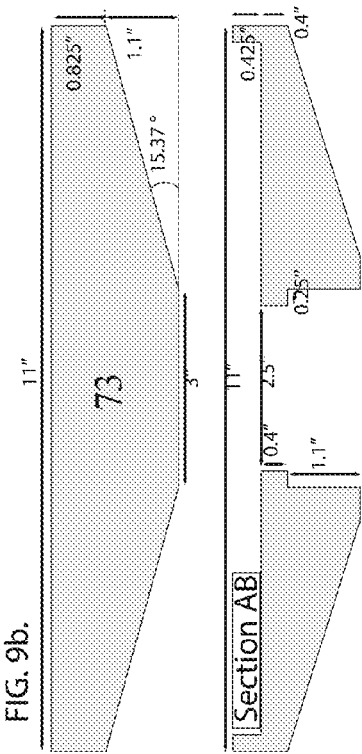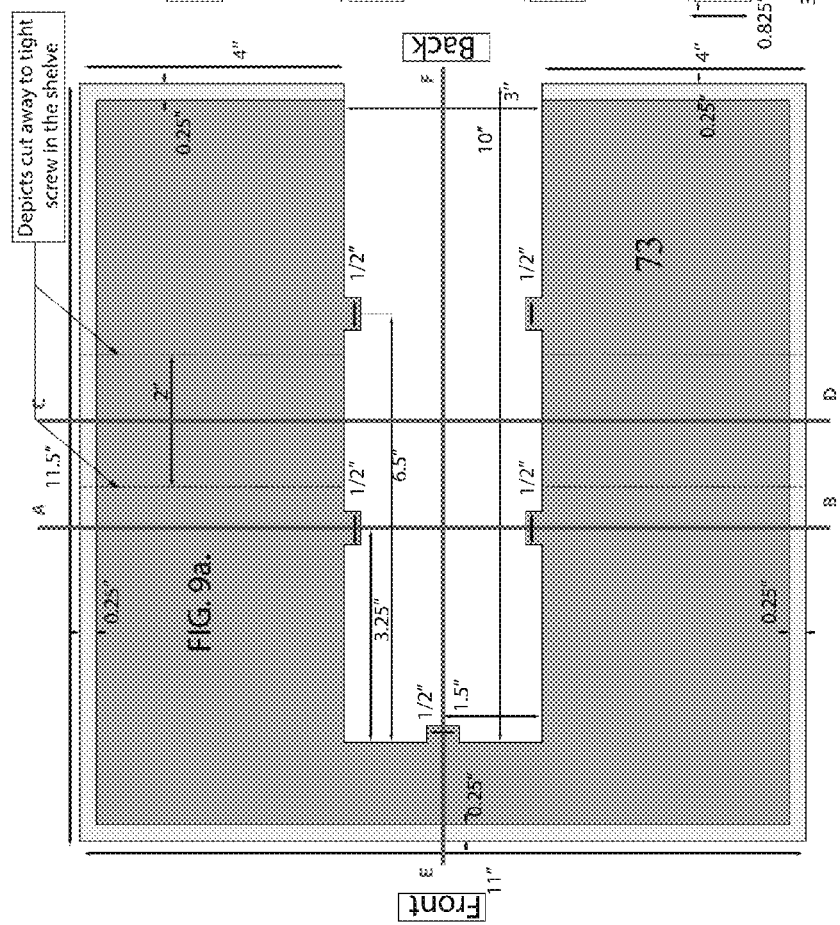

FLUOROPOLYMER PNEUMATICALLY/HYDRAULICALLY ACTUATED LIQUID CHROMATOGRAPHIC SYSTEM FOR USE WITH HARSH REAGENTS

PRIORITY

This utility application claims the benefit of U.S. Provisional Patent Application No. 61/843,509, filed on Jul. 8, 2013, the entirety of which is incorporated by reference

BACKGROUND OF THE INVENTION

1. Field of the Invention

This invention relates to High Performance Liquid Chromatography (HPLC) and more particularly, this invention relates to a pneumatically- and/or hydraulically-actuated preparation and purification method and system that operates in harsh environments and with harsh reagents.

2. Background of the Invention

Enhanced chromatographic techniques are required for investigations in biosciences, environmental sciences, nuclear chemistry and geochemistry. Traditional gravity driven (open column) chromatography, while clean and corrosion resistant, suffers from significant limitations pertaining to the overall length of column and resin size, and are time inefficient as they require multiple passes in order to achieve adequate separation of constituents (e.g., Ni and Mg).

High-performance liquid chromatography (HPLC) overcame many of these limitations (e.g., a closed-system setup involving the ability to pressurize the system, which allows for longer columns, finer resin-size and better separations; basically a semi-automated set-up). However, they are not sufficiently corrosion resistant and are thus not suitable to handle the highly corrosive reagents necessary to effect clean separations of certain compounds and elements. Two major causes of problems are the following: 1) the liquid flow path often contains glass, metal or non-resistant plastic parts that are corroded/dissolved by concentrated acids or organic solvents, leading to contamination of the samples, and 2) the electronic controls are often in close spatial relationship with the HPLC unit, drastically shortening the lifespan of the apparatus as the metallic parts rapidly corrode in these harsh chemical environments.

Some gas chromatographs use pressure as both the actuation medium and the signal to trigger the next step of the process in a force-feedback reaction chain in order to isolate one or more desired gas species from bulk gas. A motivation to such developments was avoiding explosion of flammable gases in contact with an ignition source. In such systems, the sample and carrier gases flow under their own pressure, they mix spontaneously, and only one inert carrier gas is used at once. Also, many of these systems rely on a complex assemblage of interconnected "logic elements" (e.g., metal-based mechanical parts producing various output signals from respective inputs signals). It is this assemblage that is susceptible to corrosion and other harsh environs of HPLC protocols.

Liquid chromatographic separation processes are often performed in laboratory spaces where fumes of corrosive solvents are permanently present, thus containment of the separation columns alone do not protect the electronic units or any exposed parts that are not chemically resistant. Moreover, the processing schemes are more complex in liquid chromatography than in gas chromatography, in that several corrosive liquid reagents often have to be used in combination, pumped with a precise mixing proportion, actively mixed through stirring or other means to overcome differences in densities and viscosities, and forced through the column by means external to the liquid of interest. The eluents are often chemically and/or physically unstable, requiring timely and frequent preparation. Due to this complexity, HPLC systems necessitate sophisticated computer software that offer more flexibility to rapidly modify elution characteristics, rather than logic elements hardware used in pneumatic gas chromatography.

A need exists in the art for a High Performance Liquid Chromatography method and system which can withstand highly corrosive reagents and operating environments. The method and system should rely on as few electronic components as possible so as to minimize corrosion damage to the components, yet should be apt to full automation via computer software.

SUMMARY OF INVENTION

An object of the invention is to provide an HPLC system and method that overcomes many of the disadvantages of the prior art.

Another object of the invention is to provide an HPLC system and method that is resistant to typical harsh environments and reagents associated with some elemental separation protocols. A feature of the invention is the use of pneumatic/hydraulic actuation. An advantage of the invention is that all metallic parts are removed from the proximity of the flow path of potentially harsh chemicals, thereby extending the lifetime of HPLC systems componentry.

Still another object of the present invention is to provide an HPLC method and system that uses pneumatically/ hydraulically actuated valves, pumps, sample injection loops and X-Y stages. A feature of the invention is that these components are actuated via fluid flow instead of through electronics. An advantage of the invention is that any electronics associated with the invented method and system are further isolated from the HPLC system, and specifically, the electronics of the invented system are isolated from the flow path and instead encapsulated in a positively pressured and corrosion resistant enclosure.

Briefly, the invention provides a high-performance liquid chromatography system, said system comprising a reagent reservoir or a plurality of reagent reservoirs, wherein the reservoir contains a temperature control means; a mixing chamber or a plurality of mixing chambers which contains a temperature control and stirring means, wherein the contents of the reagent reservoir(s) are combined; a pump, or a plurality of pumps, that transfers the contents of the at least one reservoir to the mixing chamber(s); a sample injection system, or a plurality of injection systems that allows injection of the sample in a modular elution column, or a plurality of modular elution columns, wherein the modular elution column(s) contains a temperature control means, wherein the length of the column and the volume of the elution collection reservoirs can be adjusted, and an X-Y moving stage or manifold that can direct eluted volumes to a plurality of liquid receptacles, wherein all moving components of the said system are pneumatically- or hydraulically-actuated.

The invention also provides a sample injection loop comprising a housing defining a first means of ingress and a first means of egress; a first body concentrically arranged within said housing, said first body in rotatable communication with said housing; a plurality of separate passageways integrally molded within said first body wherein each of said passageways as a first end that terminates in a means of ingress and further wherein each of said passageways has a second end that terminates in a means of egress; and a sample storage conduit having a first end in fluid communication with the means of egress of one of said passageways and a second end in fluid communication with the means of ingress of another of said passageways.

BRIEF DESCRIPTION OF DRAWING

The invention together with the above and other objects and advantages will be best understood from the following detailed description of the invention shown in the accompanying drawings, wherein:

FIG. 1C, parts Ca-Cc, show a schematic of a mixing chamber, in accordance with feature of the present invention;

FIG. 1E is a schematic of a pneumatic all plastic sample injection loop, in accordance with features of the present invention as depicted in FIG. 1B;

FIG. 1F is a schematic showing the functioning of the sample injection loop shown in FIG. 1E;

FIG. 1G is a schematic of a pneumatically actuated, all plastic X-Y moving stage, as depicted in FIG. 1B;

FIG. 2 is software code related to the pump solenoid status (on or off), in accordance with features of the present invention;

FIGS. 7A-E depict different views of a device depicted in FIG. 1A for moving and supporting an eluent receiving manifold, in accordance with features of the present invention;

FIGS. 8A-E depict complementary components of the device depicted in FIG. 7 for moving and supporting an eluent receiving manifold, in accordance with features of the present invention; and FIG. 9A-B is a support structure for sample collection containers, such as beakers, in accordance with features of the present invention as depicted in embodiment one in FIG. 1A.

DETAILED DESCRIPTION OF THE INVENTION

Figure 1A:
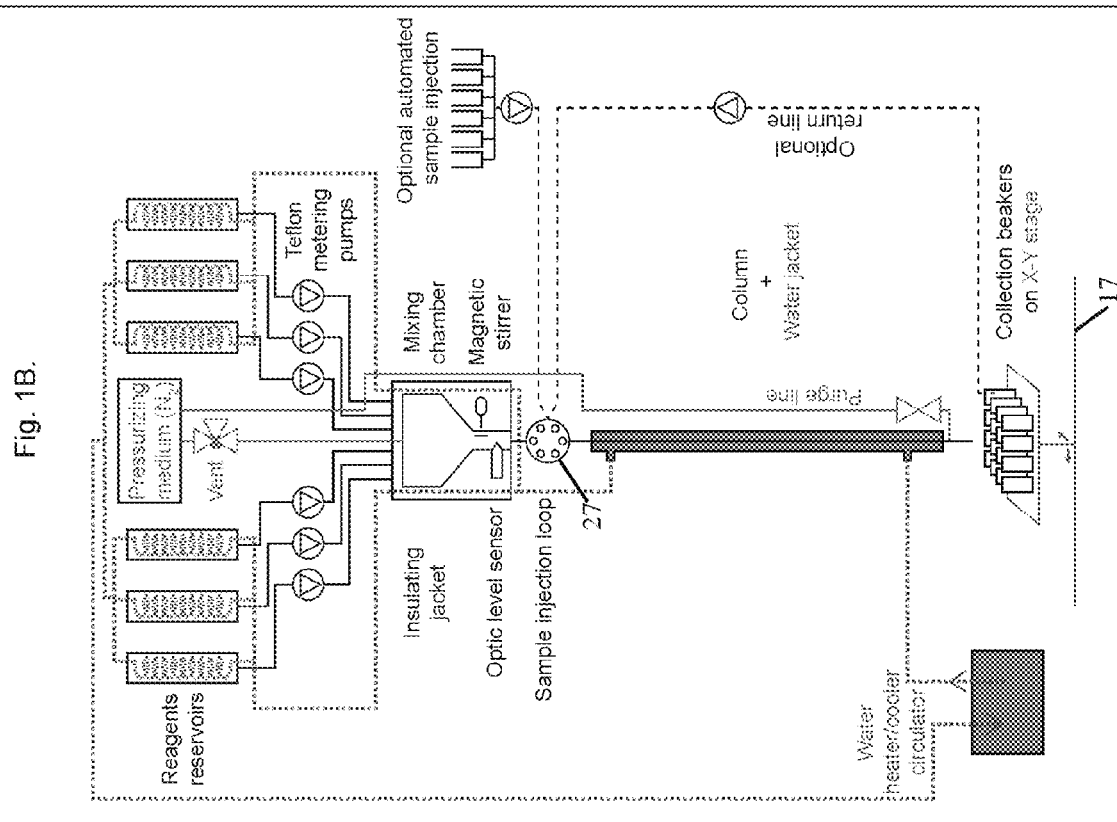
FIGS. 1A and 1B are schematic views of two main embodiments of an HPLC system, in accordance with features of the present invention.

The foregoing summary, as well as the following detailed description of certain embodiments of the present invention, will be better understood when read in conjunction with the appended drawings.

As used herein, an element or step recited in the singular and preceded with the word "a" or "an" should be understood as not excluding plural said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

The invention provides for a fully automated preparation and purification system. The system is capable of performing gradient/ramp elutions. It is modular in design so as to be adaptable to different chromatography requirements. Temperature of the parts of the system can be individually controlled from a temperature range from approximately between −55° C. and 200° C. The higher temperature range is achievable when fluids (e.g., nonaqueous fluids, polar fluids, nonpolar fluids) having boiling points higher than water are utilized. A preferred temperature range is between approximately 0° C. and 120° C., and most preferred range is approximately between 15° C. and 80° C.

Features that set the PF-HPLC system apart from state of the art chromatography configurations include the following: 1) a fluid flow path enclosed entirely (or otherwise physically isolated from ambient environment so as to prevent fluid communication with the ambient environment) by a fluoropolymer (e.g., PTFE and PFA teflon), 2) fully- or substantially-automated elution schemes controlled through software (such as LabView®, manufactured by National Instruments Corporation, Austin, Tex.), which allows for fresh mixing of reagents for each elution step, and fine scale gradient/ramp elutions, 3) temperature control of the entire system (up to about 200° C., preferably up to about 120° C. and most preferably up to about 80° C.) for enhanced chemical separations, 4) a modular design making the system easily adaptable to a variety of separation schemes, 5) the positioning or otherwise locating of substantially all of the electronics in a positively pressurized, corrosion resistant housing or enclosure that is remotely situated (e.g., physically removed and/or otherwise isolated) from the flow path so as to not be in direct fluid communication with the flow path or the fumes permanently present in the ambient environment (e.g., the laboratory environment, industrial shop floor, refinery control room, etc. . . . ) as well as those emanating from the system, 6) the provision of a system of moving shelves to accommodate various column lengths and elution receptacle sizes and 7) a means for causing the system to be actuated via fluid pressure (e.g., pneumatically or hydraulically).

In an embodiment of the invention, liquid is forced through the elution column by pressurization of the mixing chamber. For example, the mixing chamber is pressurized when filled with a pressurized dry inert gas (e.g., helium, argon,) or a relatively (compared to the reagents) nonreactive fluid, (e.g., nitrogen, carbon dioxide). It is suitable for the inert gas or the nonreactive fluid to be, cleaned, filtered, or otherwise separated from any entrained particles larger than about 0.06 microns (μm) (and preferably of any particles larger than about 0.03 μm) for example with a filter (e.g., about a 0.003 μm PTFE filter).

These features of the invented system enable its operation as a sample preparation and purification system. In the invented system, the incorporation of liquid chromatography categorizes the configuration as preparation and purification equipment with an objective of isolating or otherwise separating elements and compounds from one another with the highest yield and the lowest contamination possible. The invented system can process a sample several times in order to achieve much greater purification of the fraction of interest (orders of magnitudes). This multi-processing can be effected by manually reloading a once passed through sample through the system again, or else automatically whereby a return line routes the once passed through sample from the collection point to the beginning of the column after adjustment of the reagent strength and/or composition.

These features of the invention differentiate it from state of the art systems, which either handle (1) liquids (as in HPLC) but have electric and corrosion-prone actuators close to the flow line or (2) gases (as in pneumatic gas chromatography) but are not capable of precisely delivering and mixing multiple corrosive liquid reagents.

Actuation of the system could be made with a fluid (i.e., gas or liquid). As such, both pneumatic and hydraulic actuations are enabled by the invention. In embodiments where liquid is used as the actuation fluid, gas is used to pressurize the mixing chamber and push the liquid through the column. Preferably, pressure is the only actuation medium utilized in the system. This feature allows electronic components to be removed from conduits through which reagents flow. Suitable pneumatic pumps are comprised of corrosion-resistant materials such as fluoropolymers (e.g., Teflon®), or similar materials, which are capable of a large number of actuations. For instance the pumps are rated for approximately 25 million strokes, valves and manifolds for at least 1 million actuations and the sample injection loop and X-Y stage for at least 400,000 actuations. (These performance values are provided by the manufacturers.)

Another feature of the invented system is that internal surfaces of the reservoirs, mixing chamber and elution chamber are fabricated out of or coated with fluoropolymer. Also, substantially all connections conduits and fittings are fabricated out of, or coated in fluoropolymer, or fluoropolymer filled with high purity carbon or carbon fiber. (e.g., the mixing chamber is made of carbon-filled fluoropolymer to provide a nonreflective surface to the optical Teflon level-sensor 25; fluoropolymer filled with carbon fiber results in a strengthening of the part, which leads to a minimization of deformation under load).

The system and method is operational at a wide range of temperatures.

A suitable operational temperature range is between about −55° C. and about 200° C., and is adaptable to the requirement of the separation. A preferable temperature range is above 0° C. and below 120° C. Typical temperatures are between about 15 and about 80 degrees ° C. In an embodiment of the invention, both the heating of the reservoirs and the elution column occurs within the same closed circuit or fluid pathway. The system utilizes a variety of fluids for a heat exchange medium, including, but not limited to water, oil, emulsions or combinations thereof.

Hardware Detail

FIGS. 1A and B are schematics depiction of two embodiments of the invented system designated as numeral 10. These embodiments allow either batch or continuous operation of the system. The system comprises at least one, but typically a plurality of reagent reservoirs 11 in fluid communication with at least one mixing chamber 12 (or a plurality of mixing chambers). Situated downstream from the mixing chamber is at least one elution column 14 (or alternatively a plurality of columns) adapted to receive the mixture created in the mixing chamber.

A manifold 16 or X-Y stage 17 for separation/collection of product is positioned downstream from the column(s) 14 so as to receive the eluted fractions. Downstream of the manifold or on X-Y stage is situated a means (not shown) for collecting and analyzing the eluent. Such collecting means including beakers and/or conduits for routing eluent to instrumentation for analysis, or alternatively for rerouting eluent for reprocessing. Facilitating that alternative, a return line 18 is provided for rerunning of collected product to an elution column means of ingress so as to provide a means for re-eluting the collected product to provide additional purification. This line may be further pressurized by a pump (not shown). Detail of a platform for support of the beakers is found in FIG. 9.

The manifold platform 64 (FIG. 7) provides a means for moving sample holders vertically, (i.e., in the Y axis). Specifically, the platform 64 can move vertically (up and down) by sliding on a multi-rail system 61 (FIG. 8), each rail extending in a direction that is generally perpendicular to the plane formed by the platform. For moving the platform, one loosens or tightens a T-shaped slider component slidably received along a groove formed in each rail. Tightening a thumb-screw that runs through a non-threaded hole 71 in the platform into a threaded hole in the T-shaped component pulls the T-shaped slider against the inner part of the rail 74, thus creating a strong grip. Conversely, loosening the thumb-screw releases the tension on the T-shaped slider, thus releasing the grip on the rail.

As depicted in FIG. 7, the manifold platform carries a second similar two-rail system with T-shaped sliders 72 for adjusting the height of the shelf 73 (FIG. 9) where the containers that collect the acids are positioned relative to the manifold. Tightening a thumb-screw that runs through a non-threaded hole 75 in the shelf 73 into a threaded hole in the T-shaped slider 72 pulls the T-shaped slider against the inner part of the rail 76 carved in the manifold platform 64, thus creating a strong grip. Conversely, loosening the thumb-screw releases the tension on the T-shaped slider, thus releasing the grip on the rail. In this way, the manifold platform moves vertically relative to the depending end of the column, and the shelf moves vertically relative to the manifold, thus adjusting to collection vessels of different heights.

In one embodiment of the invention depicted in FIG. 1A, a depending end 15 of the flow column 14 is in close spatial relationship to the manifold 16, the latter of which is comprised of fluoropolymer. The pneumatically-actuated fluoropolymer manifold 16, or a plurality of manifolds is positioned at the depending end 15 (i.e., the downstream end) of the column or columns. For example, a suitable manifold illustrated herein features 14 ports, allowing for separations of at least 13 elements (one port is used for waste) without tending to the system. Alternatively, all ports of the manifold can be devoted to the separation and collection of elements, at the exclusion of one of the ports used for waste.

Figure 1B:
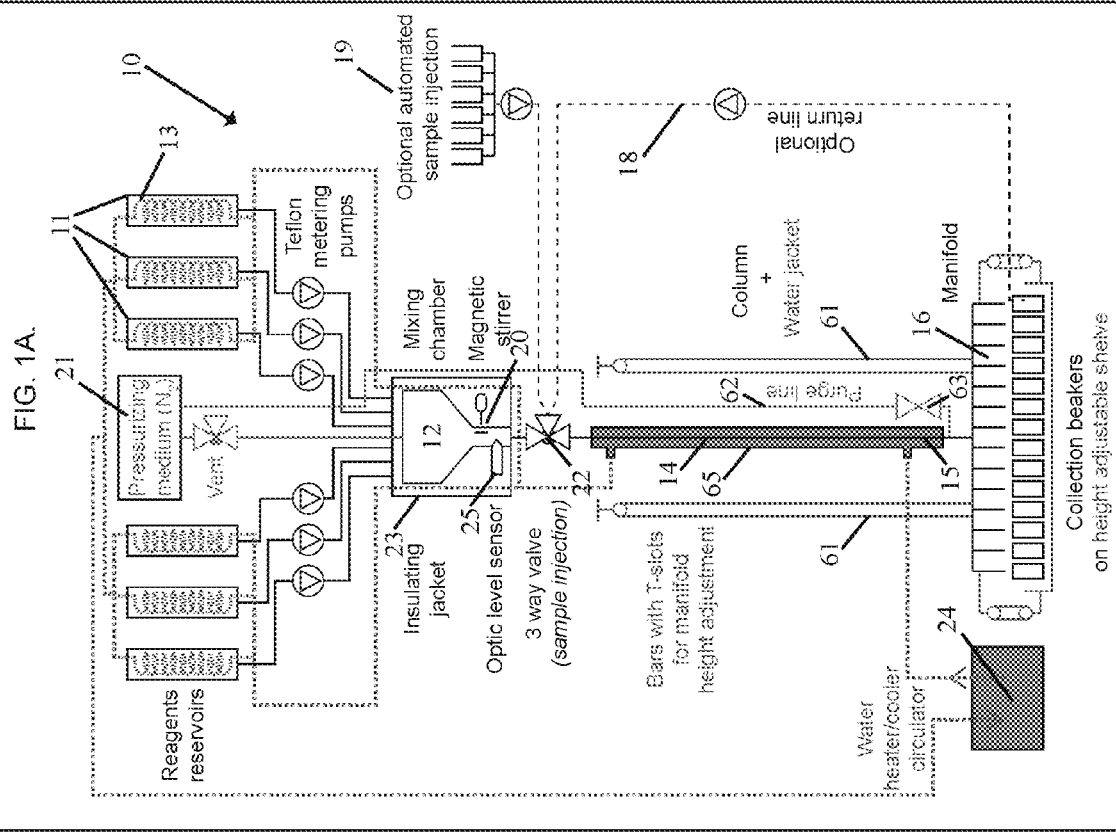

A second embodiment of the invention depicted in FIG. 1B features a pneumatic, all plastic, X-Y moving stage 17 in place of the manifold at the depending end of the column. Like the manifold, the X-Y stage allows for the automated collection of different elution fractions (which are exiting from the depending end 15 of the column) in separate receptacles. For example, a suitable X-Y stage illustrated herein (FIG. 1G) features 2 pairs of pistons, each pair 29 placed at a 90 degree angle from the other. This configuration allows the stage to stop at (or otherwise support and position a predetermined number of receptacles previously arranged in an array) under the elution column 14. For example, an embodiment of the invention enables the stage to be programmed and moved to 16 positions, thereby allowing for separations of at least 15 elements (one position is used for waste) without an operator tending to the system. Alternatively, all positions of the X-Y stage can be devoted to the separation and collection of elements, at the exclusion of one of the position used for waste.

In a preferred embodiment of the invention, the entire flow path of the system is made of fluoropolymer (e.g., PTFE or PFA), which due to its chemically inert and resistant properties is a suitable substance for the wide variety of chemicals that may be used in column chemistry.

Figure 1D:
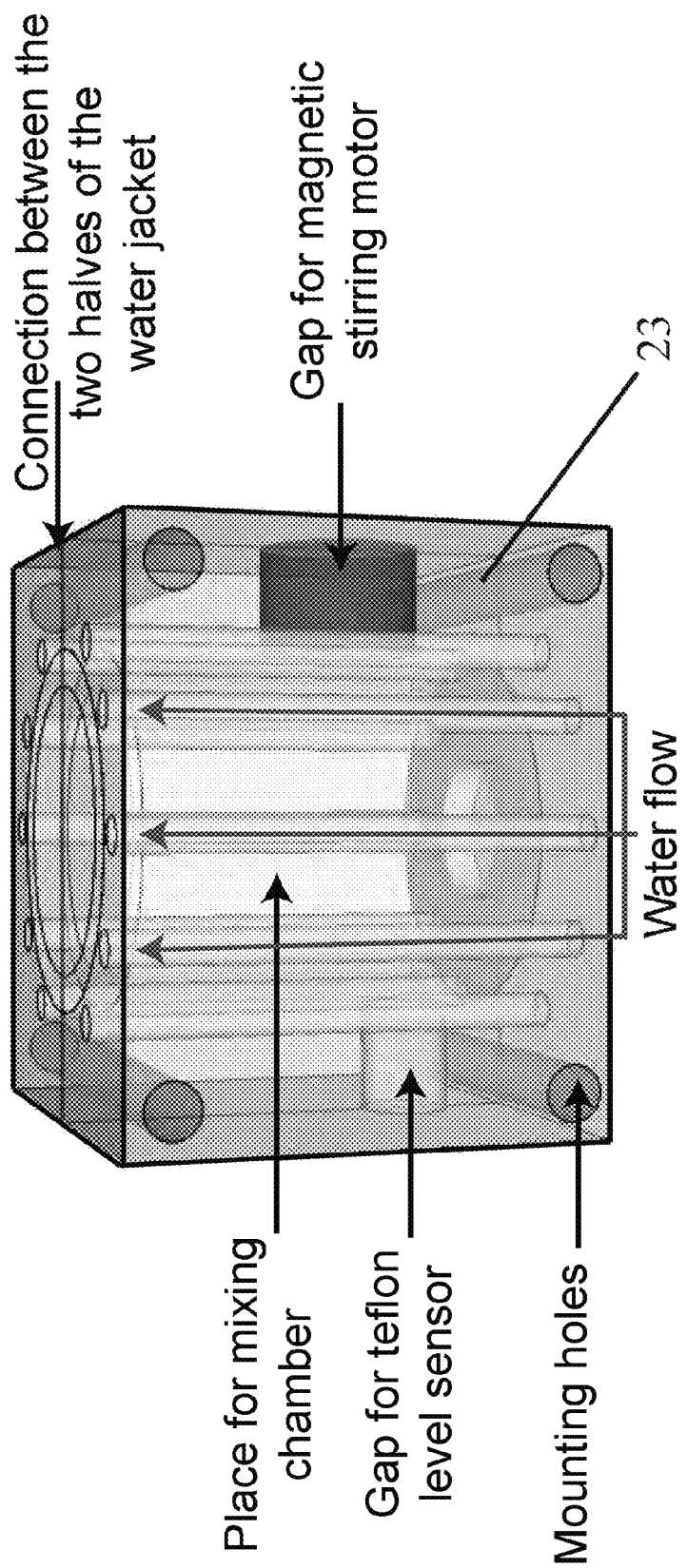
FIG. 1D is a schematic diagram of a water jacket for use with a mixing chamber, in accordance with features of the present invention.
Figure 1H:
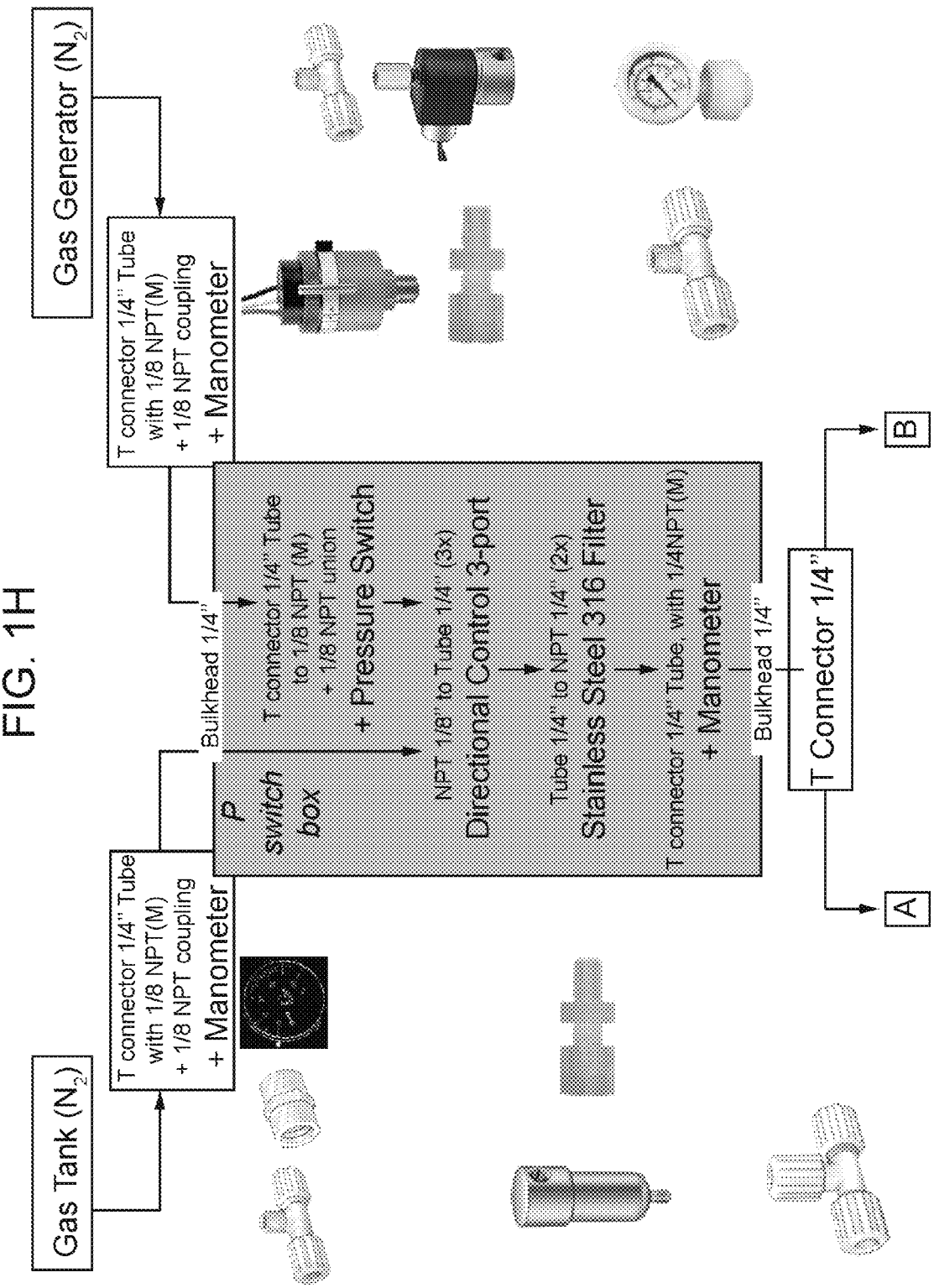
FIGS. 1H and 1I is a schematic chart of the gas flow line, in accordance with features of the present invention.
Figure 1I:
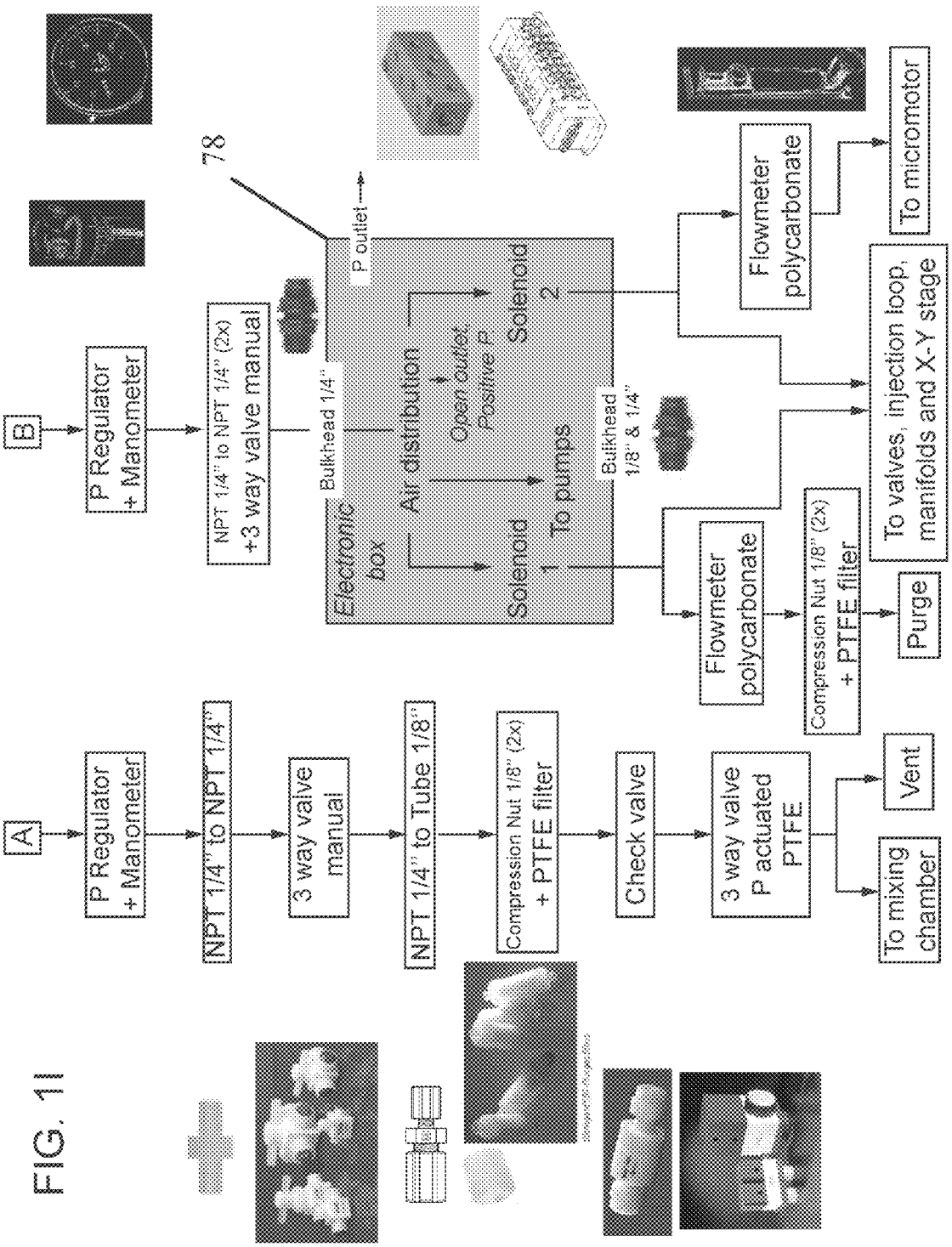

FIG. 1I depicts a remotely positioned electronics bay, box or enclosure 78, so positioned to eliminate fluid communication between the bay and the other structures of the system. All pneumatic valves, pumps, manifolds, sample injection loops, X-Y stages, and motors that are in proximity of the reagent flow path are actuated by solenoid valves located in the positively pressurized electronic bay.

A pressurized fluid (e.g., nitrogen gas) 21 injected up stream of the mixing chamber or a vacuum pump (not shown) positioned downstream of the elution column imparts positive pressure to the mixing chamber 12 after reagents are introduced via an ingress point and are mixed and homogenized in the chamber. This enables pneumatic control of the liquid flow through the system. A myriad of mixing means 20 is suitable for use in the system, including, but not limited to, a magnetic mixing bar, prop-and-shaft configurations, mixing vessel agitation, a static mixer, and combinations thereof The reagents are stored in several reservoirs. The illustrated embodiment shows the reagents are stored in up to six reservoirs 11, for example 300 mL fluoropolymer reservoirs. The walls of these reservoirs host a fluoropolymer coil 13 (depicted in dotted line), through which a heat carrying fluid (e.g., glycol, water or oil) can circulate allowing the reagent reservoirs to be temperature controlled to ensure an isothermal system. This coil 13 is charged with temperature regulating fluid and physically contacts various components of the system as a means to keep the system within a certain operating temperature.

The mixing of the reagents takes place in the mixing chamber 12, which is equipped with a liquid level sensor 25 (e.g., an optical liquid level sensor with its wetted surface made of fluoropolymer), or a weight sensor, or some other means for monitoring the volume of reagents. This mixing chamber is located inside of an insulating jacket 23 which is adapted to receive the system temperature regulating coil 13.

The flow path begins with the reagent reservoirs 11. These reservoirs can be used for any combination of water, bases, acids (e.g., $HNO_3$, HCl, HF, $H_2SO_4$, oxalic acid), organic solvents (e.g., acetone) or any other reagent required for a particular column chemistry.

In an embodiment of the invention, each of these reservoirs 11 are connected to six computer-controlled self-priming positive displacement diaphragm metering pumps. Suitable pumps are commercially available, for example from RKD Engineering, Scotts Valley, Calif. Exemplary such pumps deliver reagents into the mixing chamber 12 (pictured schematically in FIG. 1C) at a volume of between about 20 µL and about 60 µL per stroke, and typically about 40 µL, and at a rate of between about 3 to about 7 strokes per second, and typically about 5 strokes per second. In an embodiment of the system, the volume per stroke is reduced so as to achieve finer gradient elution. Also, total volume of the elution can be decreased by decreasing the column diameter. More efficient and accurate separations are the result. Since the volumes of acid, water and organic solvents introduced to the mixing chamber are carefully controlled, the eluent molarity can be similarly controlled. Though many systems are concerned with high volume throughput, it is advantageous for the described PF-HPLC system to decrease the volume per stroke delivered by the pumps in order to achieve even finer eluent molarity steps, and hence better separations. Similarly, the ability to process smaller volumes would come in handy when reducing the total elution volume (i.e., decreasing the column diameter).

Advantages of this configuration include the ability to vary acid molarities discretely on a smooth ramp in a procedure known as gradient elution in HPLC, rather than jumping in large increments from one acid molarity to another. A gradient elution typically provides better separation of compounds/elements.

Mixing Chamber Detail

The mixing chamber 12 has several novel features. A computer-monitored optical fluoropolymer level sensor, proximal to the downstream end or base of the chamber, monitors the liquid level. The volume below this sensor marks the limit of the smallest liquid pulse out of the chamber and is on the order of approximately 150-200 µL. In an embodiment of the invention, the mixing chamber is machined out of non-reflective material (e.g., carbon-filled fluoropolymer) to provide a non-reflective surface for the optical level sensor. An exemplary material is 2 percent carbon-filled fluoropolymer.

Second, a fluoropolymer magnetic stirring bar is placed upstream (i.e., above) the level sensor to ensure that reagents inside the chamber are thoroughly mixed and equilibrated prior to introduction on the column. A pneumatically actuated motor for the magnetic stirrer sits in a cavity 39 on the side of the mixing chamber, but is not in contact with any liquid directly. The cavity 39 projects medially into the housing 26 and is adapted to receive the motor magnetic stirrer.

An exemplary embodiment of the mixing chamber comprises a housing 26 adapted to substantially encapsulate a mixing chamber reservoir 28. FIG. 1C depicts a generally cylindrical shaped housing 26 within which is positioned the mixing chamber. However, other shapes are suitable.

One embodiment of the mixing chamber comprises a monolith into which is formed the mixing chamber reservoir 28 such that the reservoir is integrally molded with the housing 26. The mixing chamber reservoir 28 has a first or upstream end 30 and a second or downstream end 32. The opening of the first end 30 is closed by a lid 35 that fits snuggly in the opening and is held by o-rings. The upstream end of the lid 34 has several openings 37 that serve as ingress points for the reagents and pressurizing medium.

Another embodiment of the invention comprises the mixing chamber formed separate from the reservoir. The mixing chamber reservoir 28 has a first or upstream end 30 and a second or downstream end 32. The first end 30 of the mixing chamber reservoir 28 has a cross section that is relatively smaller in diameter than the cross section of a first end 34 or upstream end of the mixing chamber housing 26. This allows for the mixing chamber to be removably received within the housing such that the periphery of its first end 30 is substantially encircled by a lip formed by the first end 34 of the housing.

Between the first (upstream) end 30 and second (downstream) end 32 of the mixing chamber reservoir is a funnel-shaped (i.e. frusto-conical shaped) region 38 that medially converges toward the longitudinal axis of the mixing chamber. A depending end of this region 38 terminates as a conduit 36 which extends downwardly and coaxially with the longitudinal axis of the mixing chamber. A depending end of the conduit 36 defines an aperture 40.

Interior, medially facing surfaces of the frusto-conical region provides a means for directing fluid residing in the reservoir toward the conduit thereby allowing the fluid to travel through the conduit and out through the aperture 40.

The mixing chamber 12 is designed to hold pressures up to approximately 80 psi, with a lid 35 frictionally engaging with the upstream end 32 of the housing via a plurality of fluoropolymer O-rings. A medially facing surface of the periphery of the upstream end 32 of the housing defines a corresponding number of indents to frictionally nest, retain, and or otherwise engage the O-rings. The system is further sealed through an insulating jacket, positioned in close spatial relationship to the mixing chamber. Embodiments of the system include the insulating jacket in physical contact with the mixing chamber.

Once the pumps finish filling the mixing chamber reservoir and the reagents are thoroughly mixed, the chamber is pressurized via the pressurized fluid 21 (e.g., dry $N_2$ gas). A high-purity three-way diaphragm valve 22 or HPLC sample injection loop just below (i.e., downstream of) the chamber opens, provides a means of liquid ingress to the column 14. Preferably, the valve and injection loop are fabricated from or coated with substantially pure carbon-fluorine (C-F).

Using gas to pressurize the column presents two disadvantages: first, the maximum pressure that can be reached is limited to that of the supplied gas (~60 psi $N_2$ in the present embodiment) and second, the gas, if solubilized in the mixing chamber, can potentially form bubbles in the column if there is a drop in pressure or an increase in temperature in the column relative to the mixing chamber. Preferably, bubbles are to be avoided because they can hamper the flow in the column by partially occluding the fluid path, which can potentially affect the separation efficiency of the system. The issue of bubble formation is minimized by maintaining the mixing chamber at the same temperature as the column. This is facilitated by the use of the water heater/cooler circulator 24 depicted in FIGS. 1A and B, inasmuch as the same ingress and egress lines to and from the circulator 24 simultaneously thermally regulate all of the components of the system, including the column 14, the mixing chamber 12, and the reagent reservoirs 11.

The advantages of using gas to push the liquid are first, it is extremely clean, second, it offers constant pressure with time, third, it provides a means to prevent corrosion, and fourth, it minimizes the dead volume between the mixing chamber and column. In the elutions that were performed, the inventors detected no noticeable bubble formation that could hamper the flow.

Once the liquid level passes below the predetermined level sensor setting, the valve 22 shuts, the $N_2$ gas is vented to an exhaust (the vent designated as Vent on FIG. 1A) and a new stage of pumping begins. The mixing chamber 12 is designed to hold pressures up to approximately 80 psi, with the lid fitting snugly against two successive fluoropolymer O-rings. The system is further sealed through an insulating jacket, positioned in close spatial relationship to the mixing chamber. Embodiments of the system include the insulating jacket in physical contact with the mixing chamber.

The valve 22, such as a three-way fluoropolymer diaphragm valve at the base of the mixing chamber provides several functions. The first, as outlined above, is to provide a barrier from the mixing chamber to the column during reagent mixing, which can then be opened for the injection of the mobile phase to the column.

The second function, and use of the third port on the valve, is for sample introduction through a rubber septum adapted to receive a syringe (for example, a Luer lock connection). In this manner, the sample is introduced directly to the column without any concern about contaminating the mixing chamber. In the optional return line 18, a tube to thread fitting can be utilized. Two optional uses of the third port of the valve are reprocessing of collected product via the return line 18 or automated introduction 19 of at least one sample stored into at least one sample vial.

In a second main embodiment of the invention, the valve 22 is replaced by an all-plastic HPLC sample injection loop 27 (FIG. 1E). This loop was manufactured pursuant to the inventors' specifications (depicted in FIG. 1F) by International Polymer Solutions, Inc., Irvine, Calif. The loop fulfills the same role as the valve by (i) providing a barrier from the mixing chamber to the column during reagent mixing which can then be opened for the injection of the mobile phase to the column, and (2) allowing for sample injection directly into the column without any concern about contaminating the mixing chamber situated upstream from it.

The functioning of the loop is explained below and on FIG. 1F. The loop generally comprises a plurality of separate fluid paths. In the embodiment shown in FIG. 1F, three fluid paths are depicted, including a main or first conduit 42, and two flanking conduits 44 radially offset from the main conduit. All three conduits are integrally molded with a rotatable body serving as a valve body 46, wherein the main conduit 42 extends through the center of the body and through opposite ends of the periphery of the body. As such, the main conduit 42 terminates on each end by a first means of fluid ingress 48 and first means of fluid egress 50.

The valve body 46 is concentrically positioned and in rotatable communication within a valve housing 47, defining a second means of ingress 52 and a second means of egress 54. As depicted in FIG. 1F "O", these first and second means of ingress oppose each other and the first and second means of egress correspondingly oppose each other when the loop is in the "Open" position. The valve, when in the open position, allows fluid to flow from the mixing chamber reservoir 28 to the column 14.

As noted supra, the sample injection loop further comprises flanking conduits 44 positioned laterally from the centerline first conduit 42. These flanking conduits 44 are nonlinear in configuration, compared to the substantially straight first conduit 42 and terminate at one end by a third means of ingress 56 and a third means of egress 58. These flanking conduits 44 are configured so that when the third means of ingress 56 of one (a first) flanking conduit 44 forms a fluid passage with the first and second means of ingress of the valve and valve housing respectively, the third means of egress 58 of the other (a second) flanking conduit 44 forms a fluid passage with the first and second means of egress of the valve and valve housing respectively. The third means of egress 58 of the one (the first) flanking conduit is in fluid communication with the first means of ingress 56 of the other (the second) flanking conduit, via a sample coil, tube or other conduit 60, adapted to receive fluid.

FIG. 1F "I" depicts an injection configuration of the sample injection loop. In this position, the two ingress 56 means and two egress means 58 of the flanking conduits 44 enable the injection of sample solution into the sample coil 60. Once the sample traverses the coil 60, it exits out the valve via the third means of fluid egress 58 that is collinearly arranged with the means of egress 54. By switching to this "Sample injection" configuration, the loop now uses 4 ports to direct the fluid from the mixing chamber, through the tubing where the sample is stored and into the column. In this way the "I" configuration, the sample is automatically injected into the column.

FIG. 1F "C" depicts a closed configuration of the sample injection loop whereby no means of ingress are aligned with another, and so no means of egress are aligned with each other either. This configuration provides a means for preventing any exchange between the mixing chamber and the column before the reagents in the mixing chamber are fully homogenized.

The column portion of the PF-HPLC system represents another innovation. The design includes the capability of varying the column length and diameter, depending on the demands of the elemental system being studied. In an embodiment, the column comprises fluoropolymer tubing contained in a water jacket 23. Thus, by adding or removing pieces from the water jacket, and changing the length of fluoropolymer tubing, the column length and the column diameter is adaptable to any elemental system of interest. Jacket fluoropolymer pipe tubing with threaded end configurations are suitable for facilitating changing the lengths and diameters empirically determined to be necessary. Such materials are commercially available, for example through Savillex, Eden Prairie, Minn.

The column is filled with the desired resin prior to attachment to the system by letting resin beads gravitationally settle in a tube previously filled with water. Alternatively, or in addition, a vacuum box or other means is utilized to ensure that the resin is tightly packed.

After passing through the depending end 15 of the column 14, the eluted liquid volumes are collected in fluoropolymer beakers distributed through the pneumatically/hydraulically actuated fluoropolymer computer-controlled diaphragm manifold valves (16 in FIG. 1A). In an embodiment of the invention, the use of a diaphragm manifold, with 14 outlets, allows independent collection of a large number of elution cuts without the need of tending to changing vials. Alternatively, a second manifold with fewer outlets can be used for simpler elution schemes. In a second main embodiment of the system the eluted liquid volumes are distributed into fluoropolymer beakers that are positioned below the end of the elution tubing by actuating the pneumatically/hydraulically fluoropolymer computer-controlled X-Y moving stage (FIGS. 1G and 17 in FIG. 1B). The trigger for the preparation of the next elution step is a signal from the level sensor in the mixing chamber (which detects whether the chamber is empty or not).

To allow for flexibility in column length and elution receptacle volume, the downstream manifold is mounted on a platform that can be moved up and down (i.e., along the y or vertical axis) on two tracks and the beakers are mounted on a second platform that can be moved up and down relative to the manifold. Details of this platform are illustrated in FIGS. 7-9.

To improve liquid recovery and avoid stagnation of the eluted liquid volumes downstream of the column, a purge conduit 62 flushes a low-pressure inert dry gas (e.g., $N_2$, FIGS. 1A and 1B) into the tubing and components (such as the fluoropolymer manifold) downstream of the separation column. The gas is applied at the distal (i.e., depending end 15 of the column) via the actuation of a valve 63 positioned just inferior from the depending end of the column.

A further enhancement is that the whole system can be thermally controlled. Using a circulating fluid heater (24 in FIG. 1A), the inventors have designed an independent closed loop water flow that is in contact with substantially all of the components of the HPLC system. The circulation path extends from the water jacket surrounding the column, through the insulating jacket that surrounds the mixing chamber (12 in FIG. 1A), to the six fluoropolymer coils that are isolated inside of the reagent reservoirs (11 in FIG. 1A), before the water is re-circulated back to the water heater. If the heating coils are located on the outside of the reagent reservoirs, then they need not be fluorocarbon coated. FIG. 1D depicts a water jacket designed to encapsulate the mixing chamber utilized in the instant method and device.

A pressure switch ensures that the pressure of the actuating gas remains above a predetermined amount. Suitable pressures for the system range from between approximately 10 psi and 100 psi, and preferably between about 20 psi and 80 psi, and most preferably between 50 psi and 70 psi. For example, if the predetermined value is about 60 psi and the pressure drops below that value (e.g., due to power failure of the gas generator), the switch changes the gas source from the gas generator to a gas tank supplying at least about 60 psi. An example of a gas supply set-up is shown in FIGS. 1H and 1I.

Software Detail

A salient feature of the invention is the use of software to actuate the pneumatic system and method. Note that, in the interest of conciseness, the following section describes only the software controlling the main embodiment of the system described in FIG. 1A. The software controlling the second main embodiment has the same general structure and differs only in the details of the actuation of two parts: the sample injection loop and the X-Y moving stage.

The programmable system controls all aspects of the elution, including, but not limited to, introduction of the sample, pumping of the reagents in the mixing chamber to achieve a desire concentration, elution of the mixed reagents through the column, and distribution of elution cuts in collecting receptacles.

In an embodiment of the invention, a program will run a series of subprograms after determining whether input data is valid. The subprogram may correspond to one of several steps in the process. For example, step 1 may calculate the number of pump cycles (e.g., strokes) required to obtain desired total mixture volume and concentration of solvents.

The PF-HPLC system is controlled and automated entirely via software and a code designed by the inventors, so depicted in FIGS. 2-6. The application of these subroutines is visually depicted in FIG. 1C, wherein the numerals in that photograph correspond to the figure numbers embodying the code.

An embodiment of the proposed system is controlled via an external computer, running LabView software from National Instruments. LabView uses a graphical programming interface that enables the control of electric components, as well as the ability to program additional commands. Through this computer system we are able to specify an elution scheme (i.e., the mixing parameters, including the types of reagents, volumes and molarities desired), from which the program calculates the amount of liquid needed from each liquid reservoir for each step. From there, the computer program controls the pumping of the metering pumps, the mixing of reagents 13, the monitoring of the liquid level in the mixing chamber, the opening/closing of the valve or sample injection loop that leads from the mixing chamber to the column, the $N_2$ pressurization of the mixing chamber, the distribution of eluted volumes from the diaphragm manifolds or X-Y stage at the end of the column to the collecting vials, and the purging of the eluted liquid contained in the tubing and components downstream of the column. In this manner, a complex elution can be completely automated.

An initial condition for the system may begin with pump solenoids all off. FIG. 2 is a LabView sub routine for this condition. FIG. 3 is the overarching LabView software code for the embodiment of this system as depicted on FIG. 1A. FIGS. 4-6 are the sub routines called by the overarching code shown on FIG. 3. The detailed functioning of this embodiment of the software code is described further below.

Briefly, the code imports the input parameters specified by the user and assesses if these input parameters are valid. If the parameters are not valid, the sequence is aborted (FIG. 3F). If the parameters are valid, the user is asked whether the sequence should be run or not. If the user choses not to run the sequence, the sequence is aborted (FIG. 3E). If the user decides to run the sequence the code assesses if the next elution step is a "sample loading" step or not.

If the step is not a "sample loading" step, the code triggers the pumps to make the new reagent as specified in the input parameters. The mixture is homogenized by agitation and the chamber is then pressurized, which forces the mixture out of the chamber and into the elution column (FIGS. 3C and 3D). Once the liquid level reaches the level sensor at the bottom of the mixing chamber, the next elution step starts.

Figure 3A:
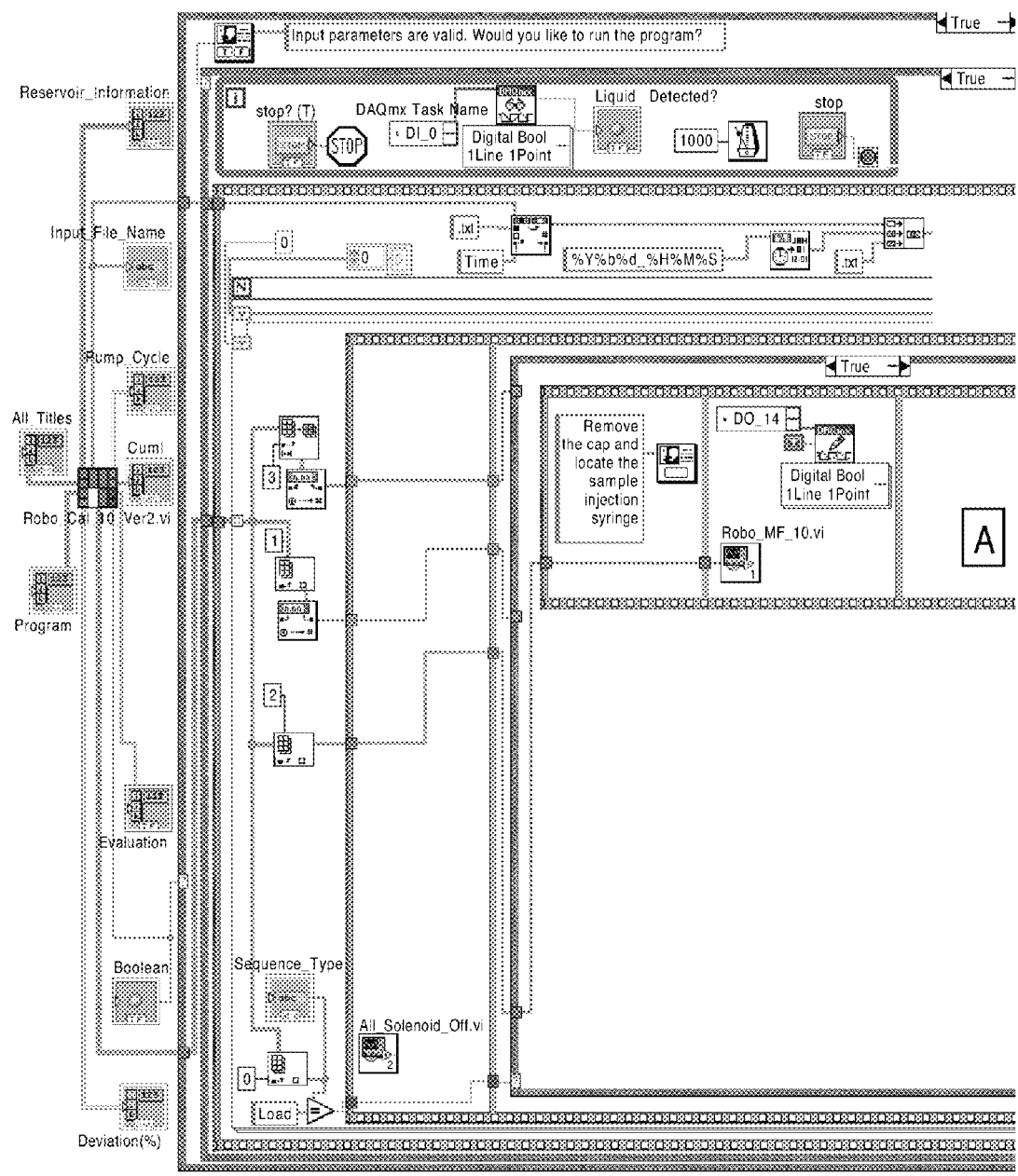
FIGS. 3A and 3B is software code for sample loading, in accordance with features of the present invention.
Figure 3B:
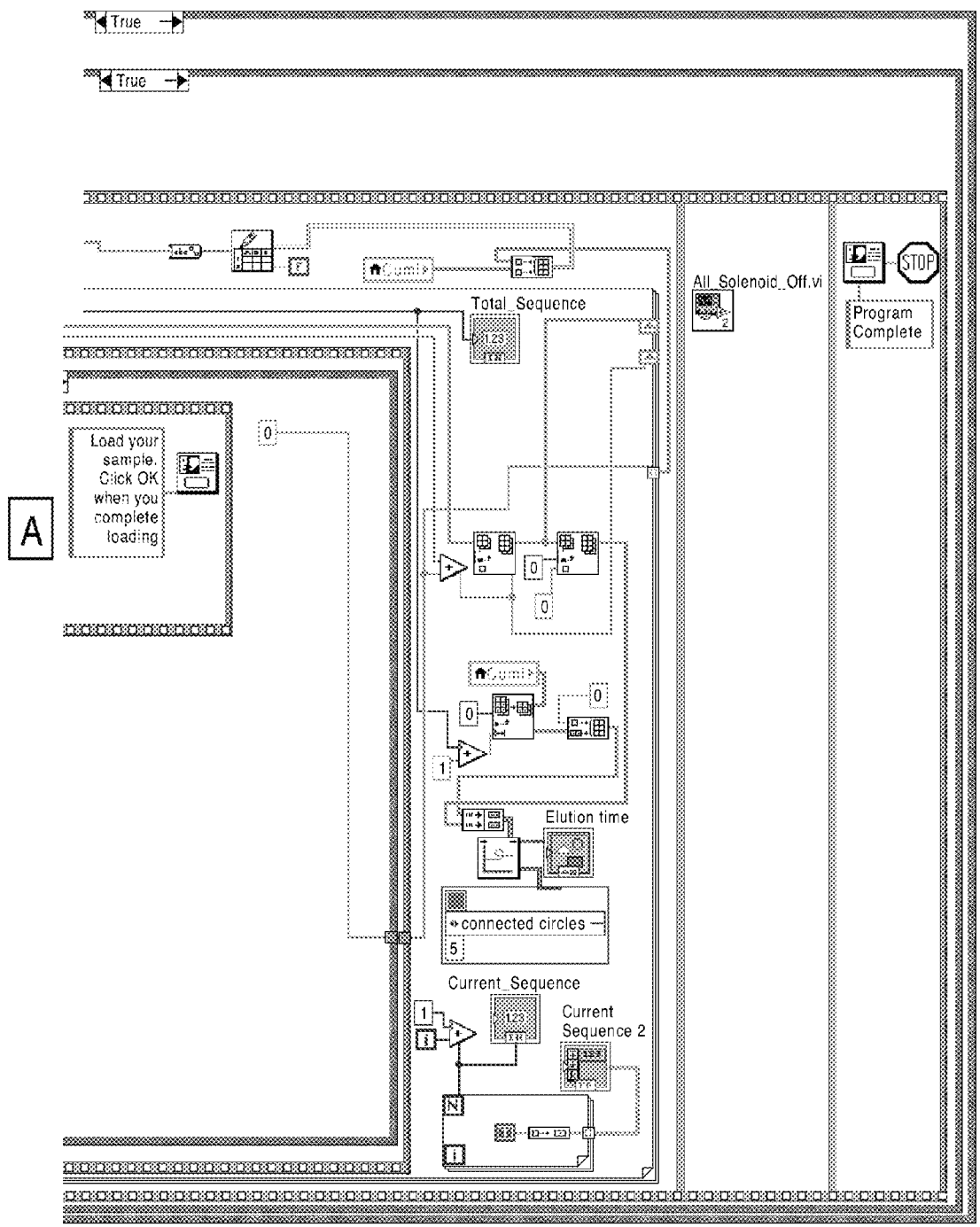
Figure 3C:
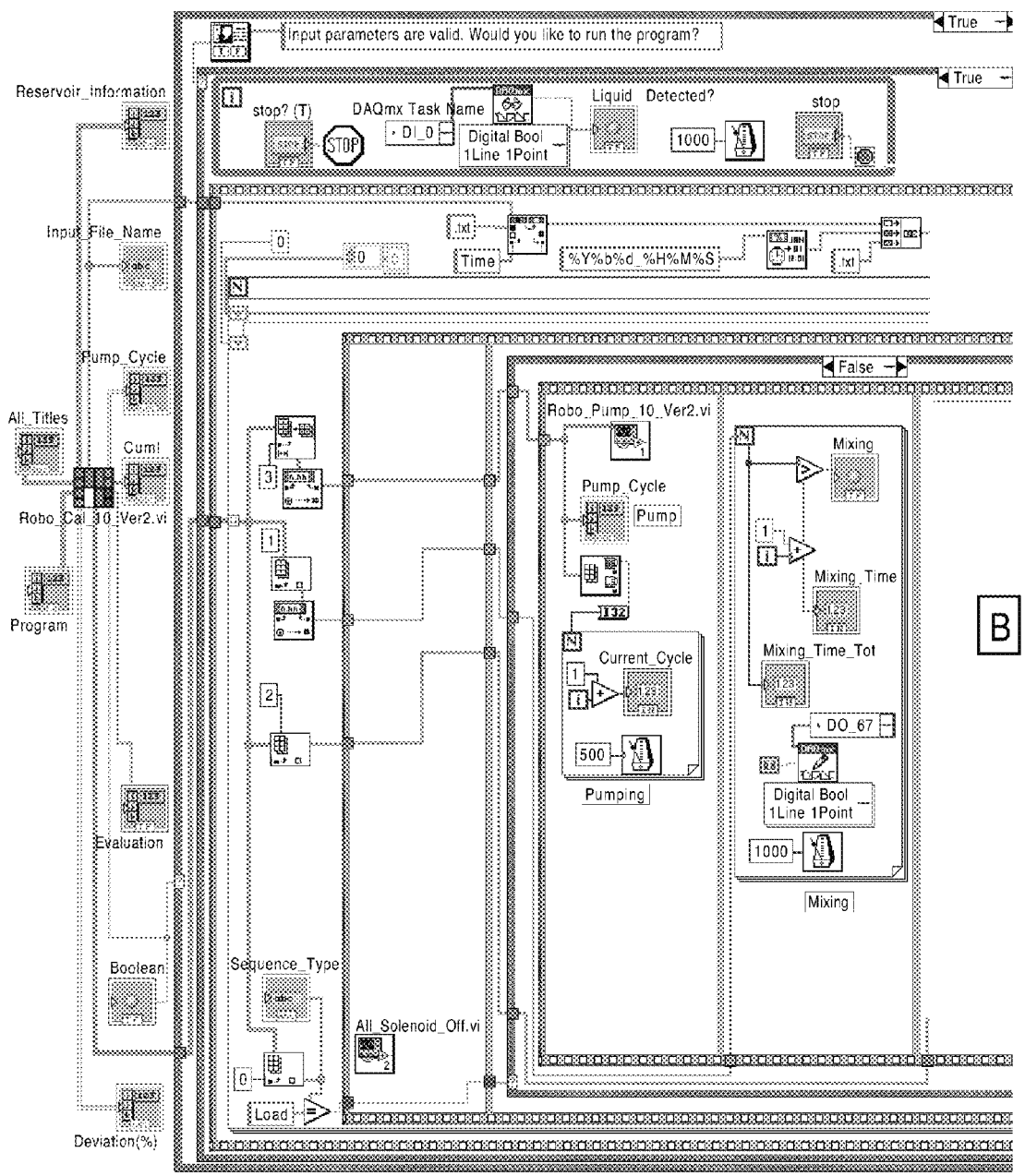
FIGS. 3C and 3D is software code for making, mixing and elution of reagents, in accordance with features of the present invention.
Figure 3D:
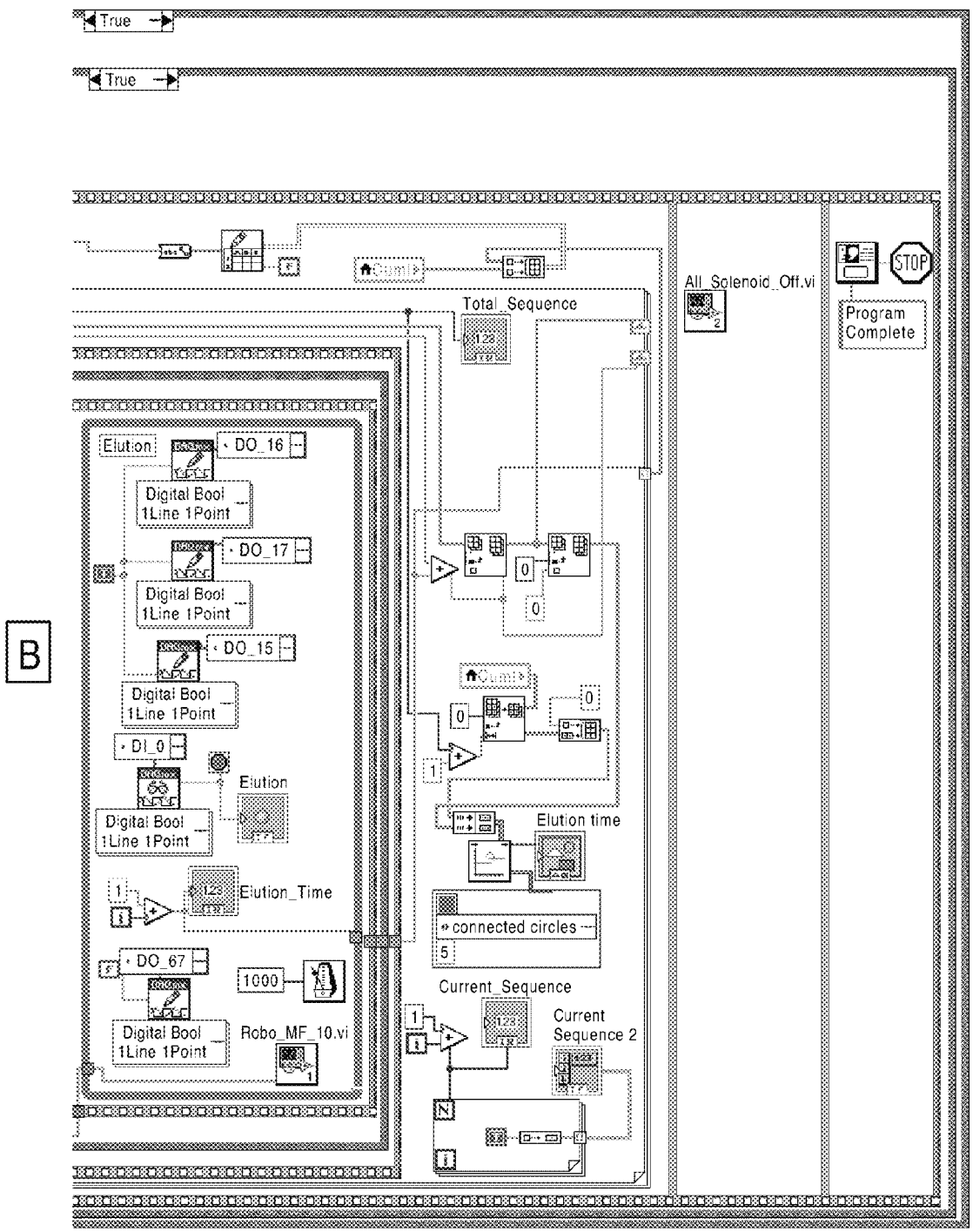
Figure 3E:
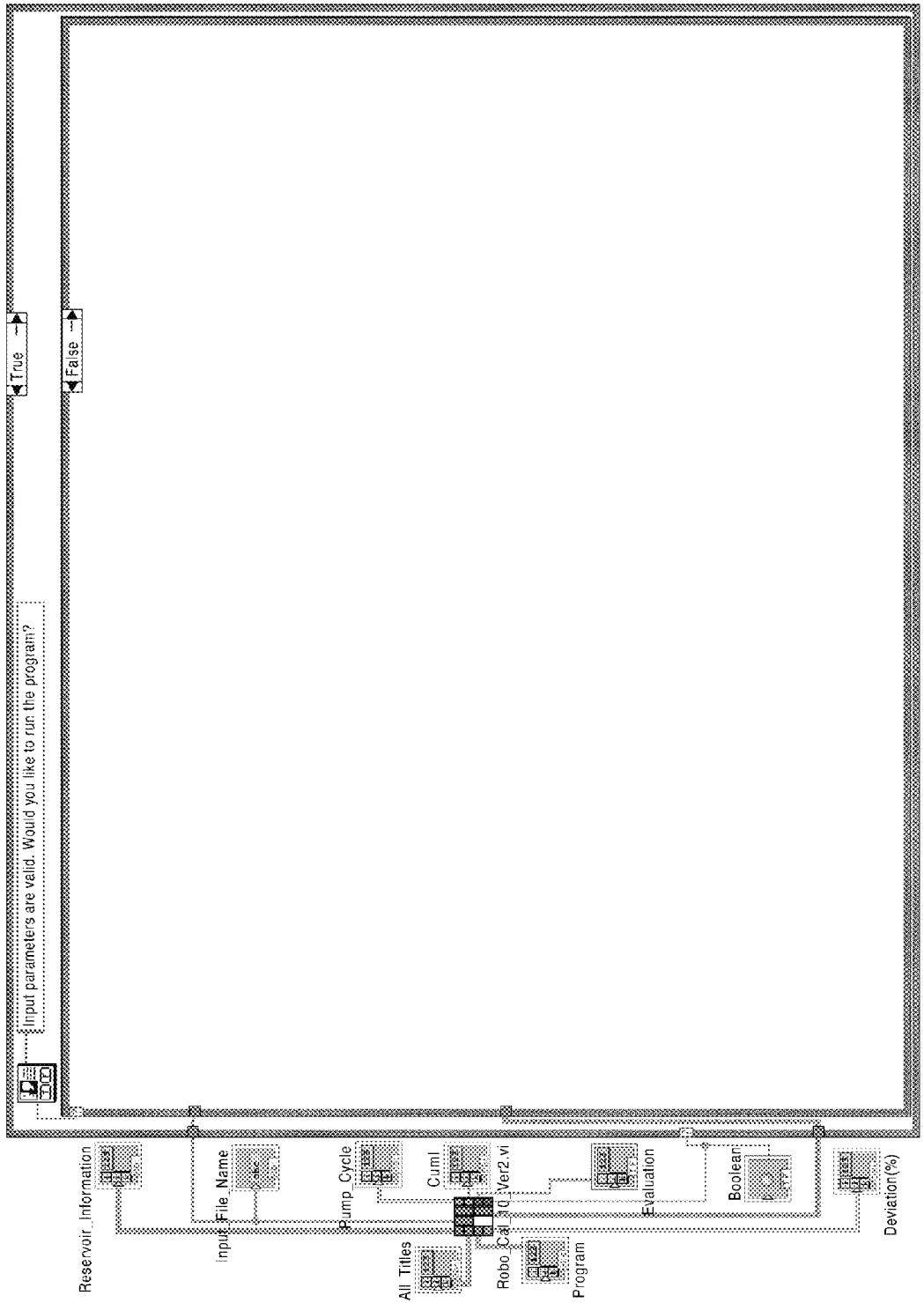
FIGS. 3E and 3F are software addressing input parameters, in accordance with features of the present invention
Figure 3F:
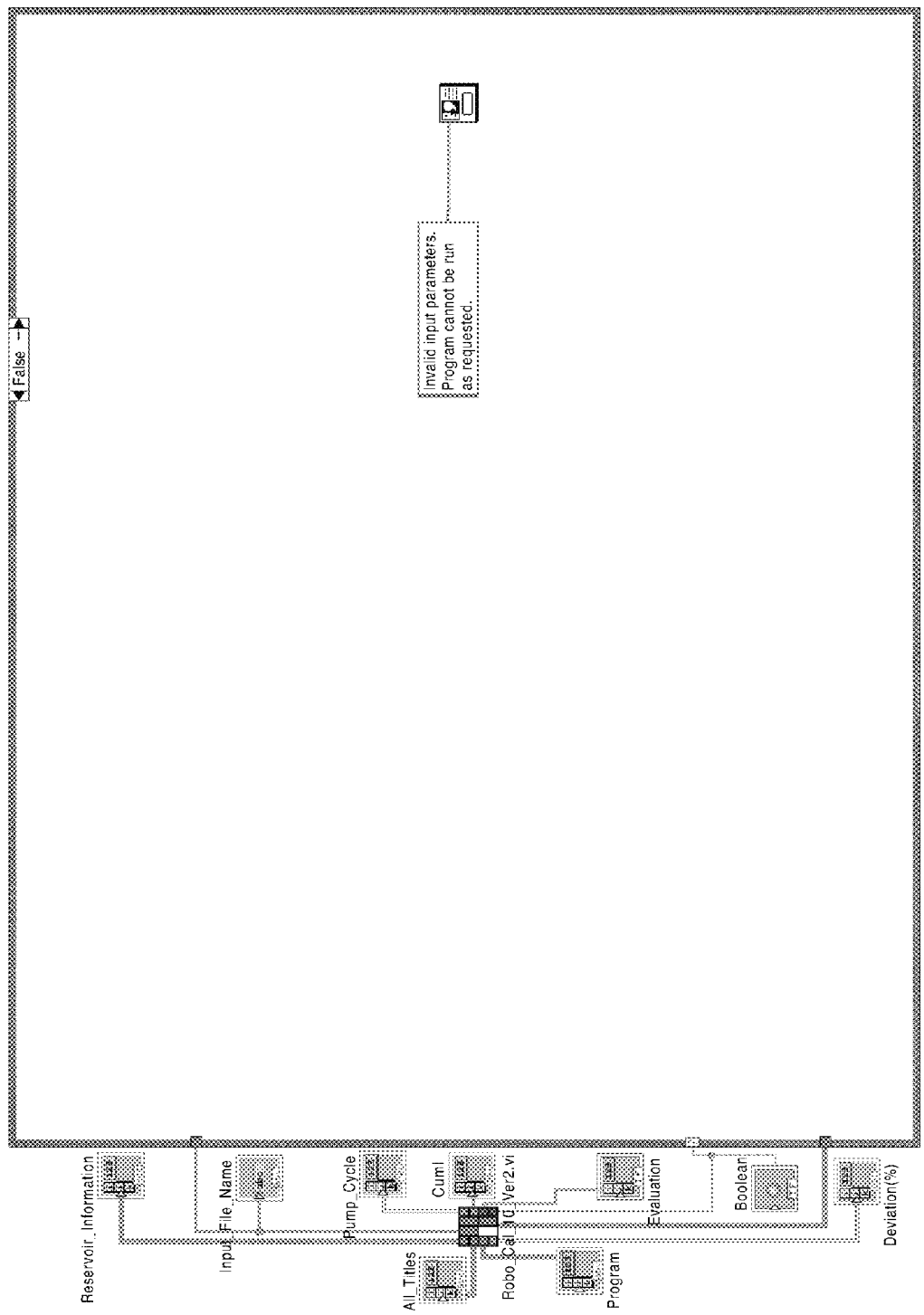
Figure 4:
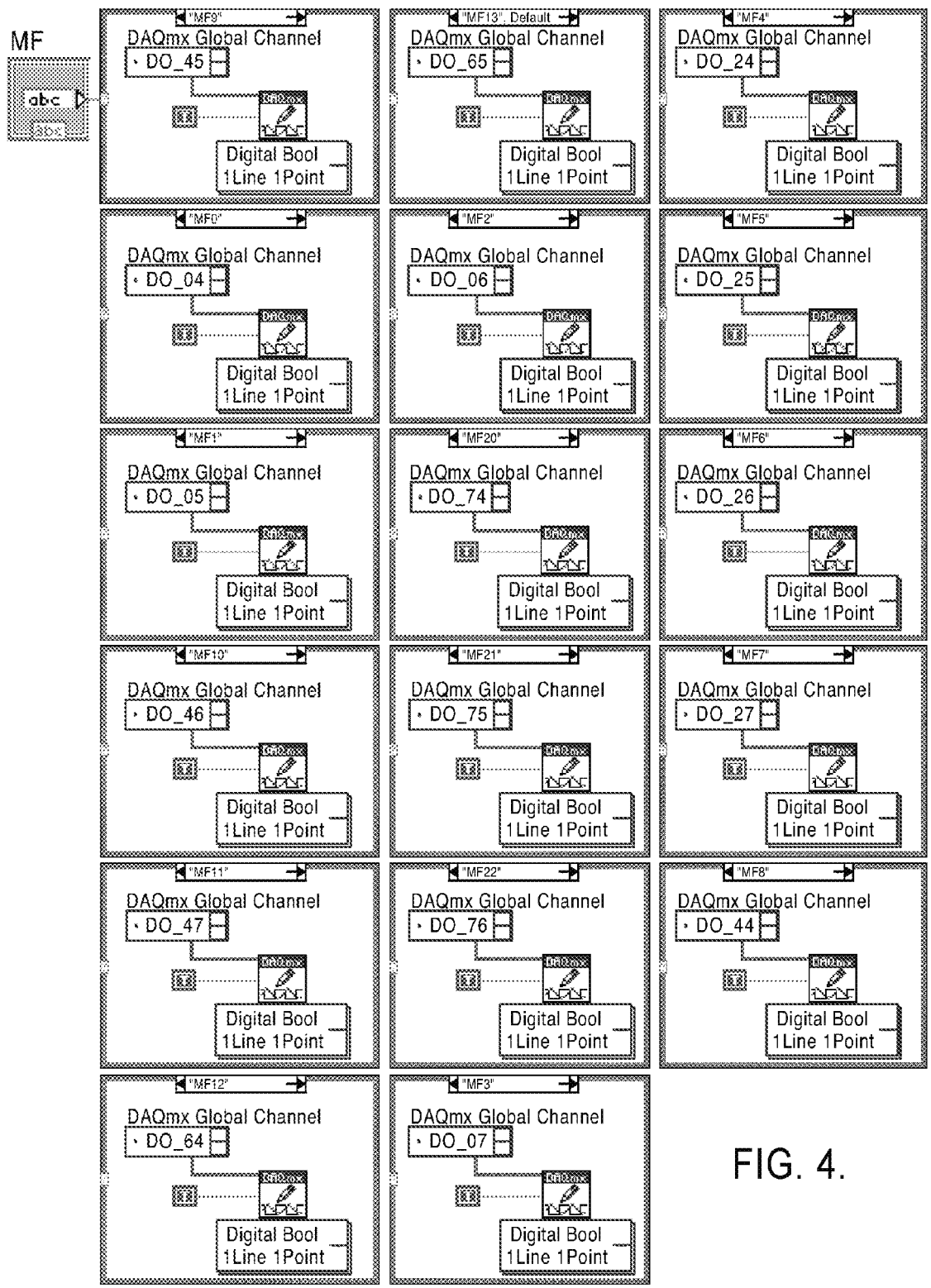
FIG. 4 is software code for monitoring and actuating the product collection manifold which is situated at the end of an elution column, in accordance with features of the present invention as depicted in FIG. 1A.
Figure 5A:
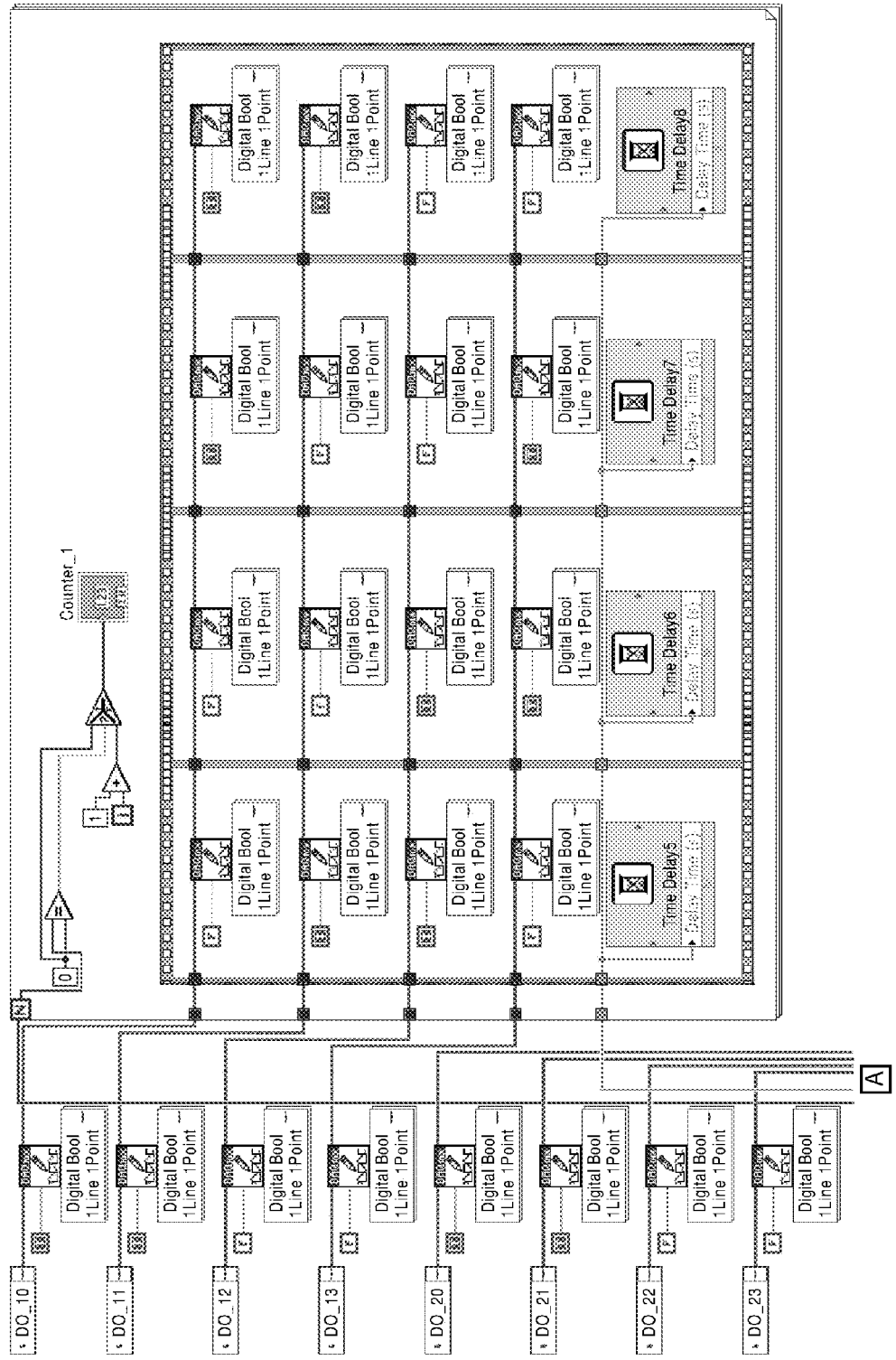
FIGS. 5A-F depict software code controlling and depicting status of the pump(s) utilized in the system, in accordance with features of the present invention.
Figure 5B:
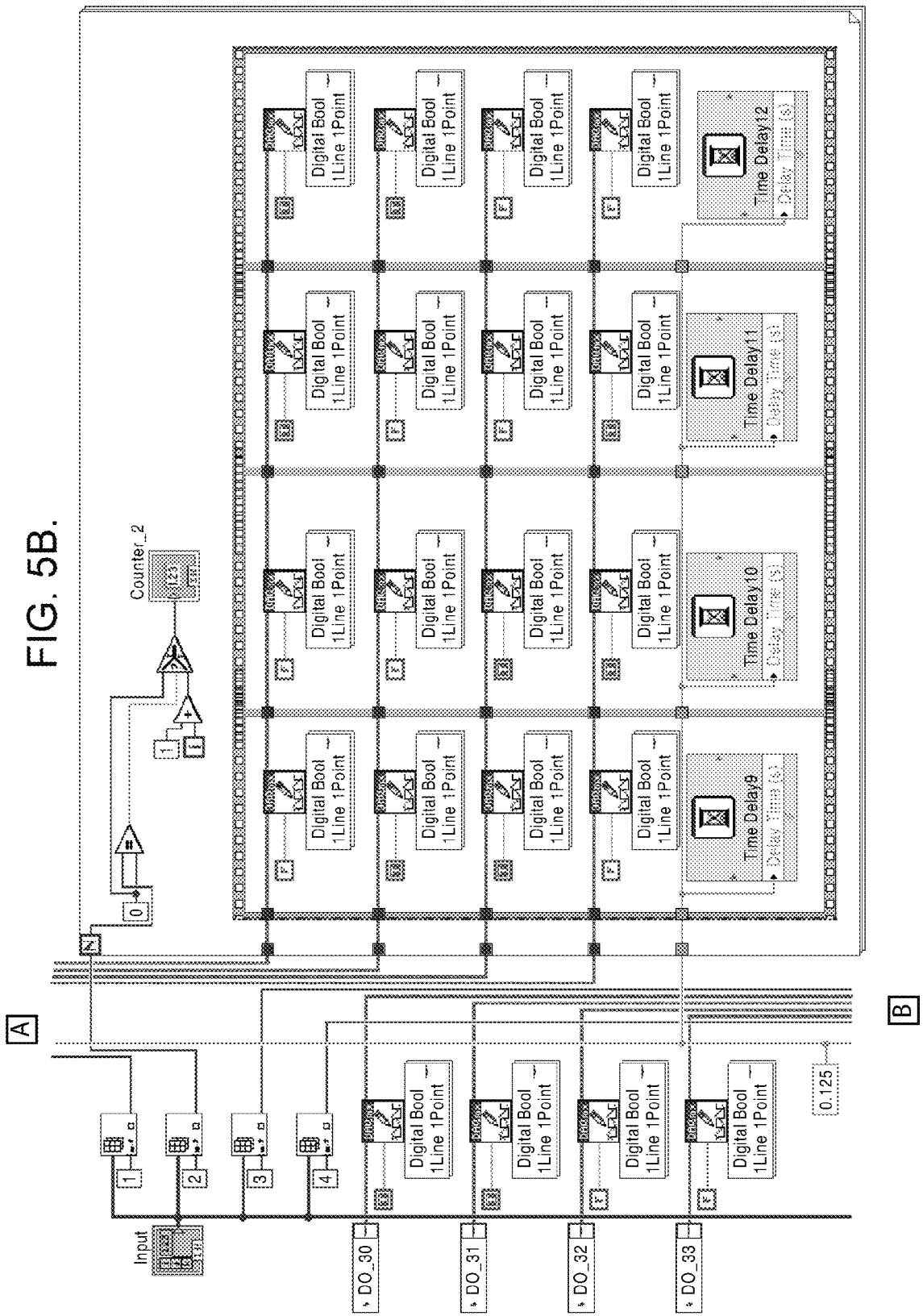
Figure 5C:
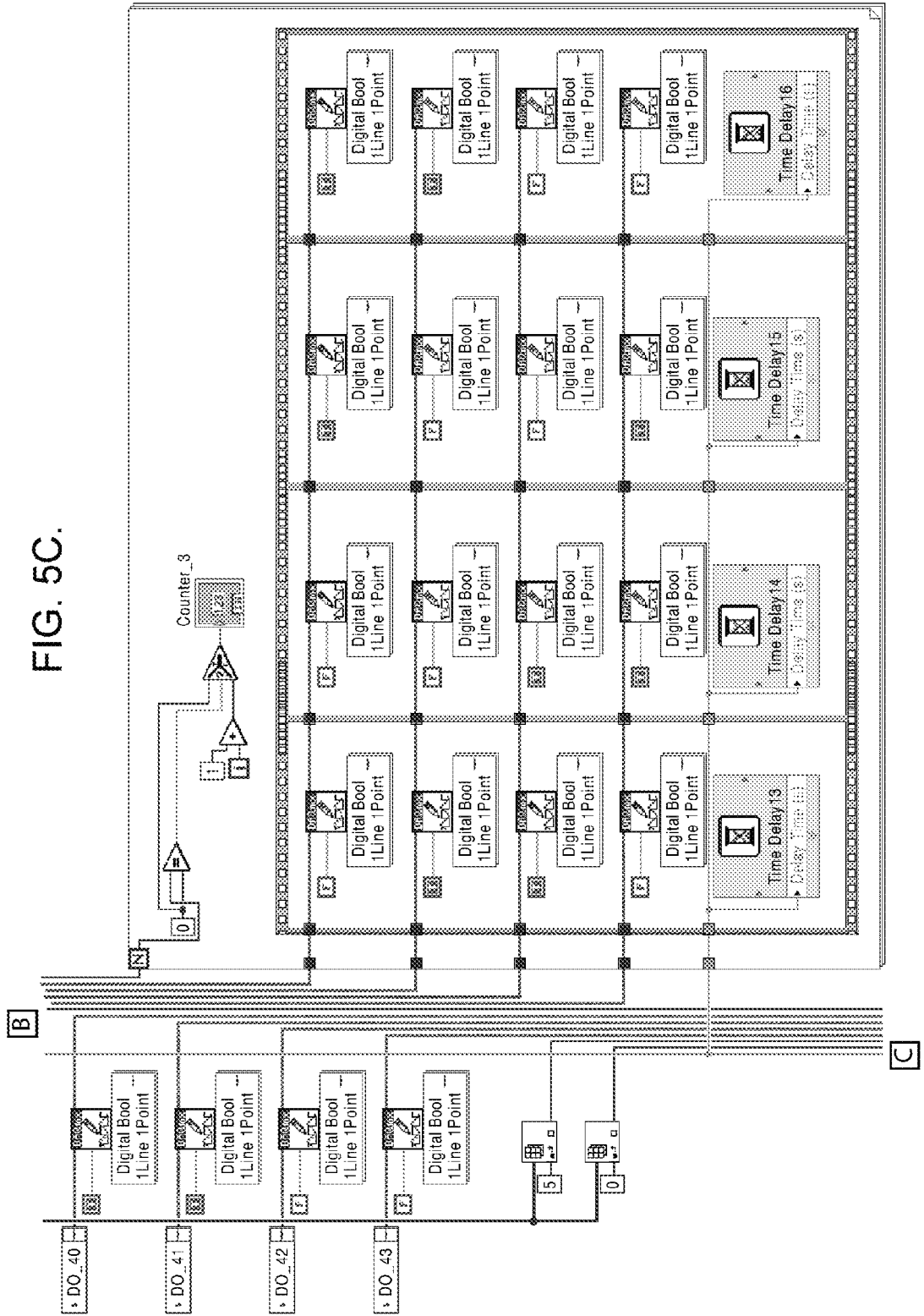
Figure 5D:
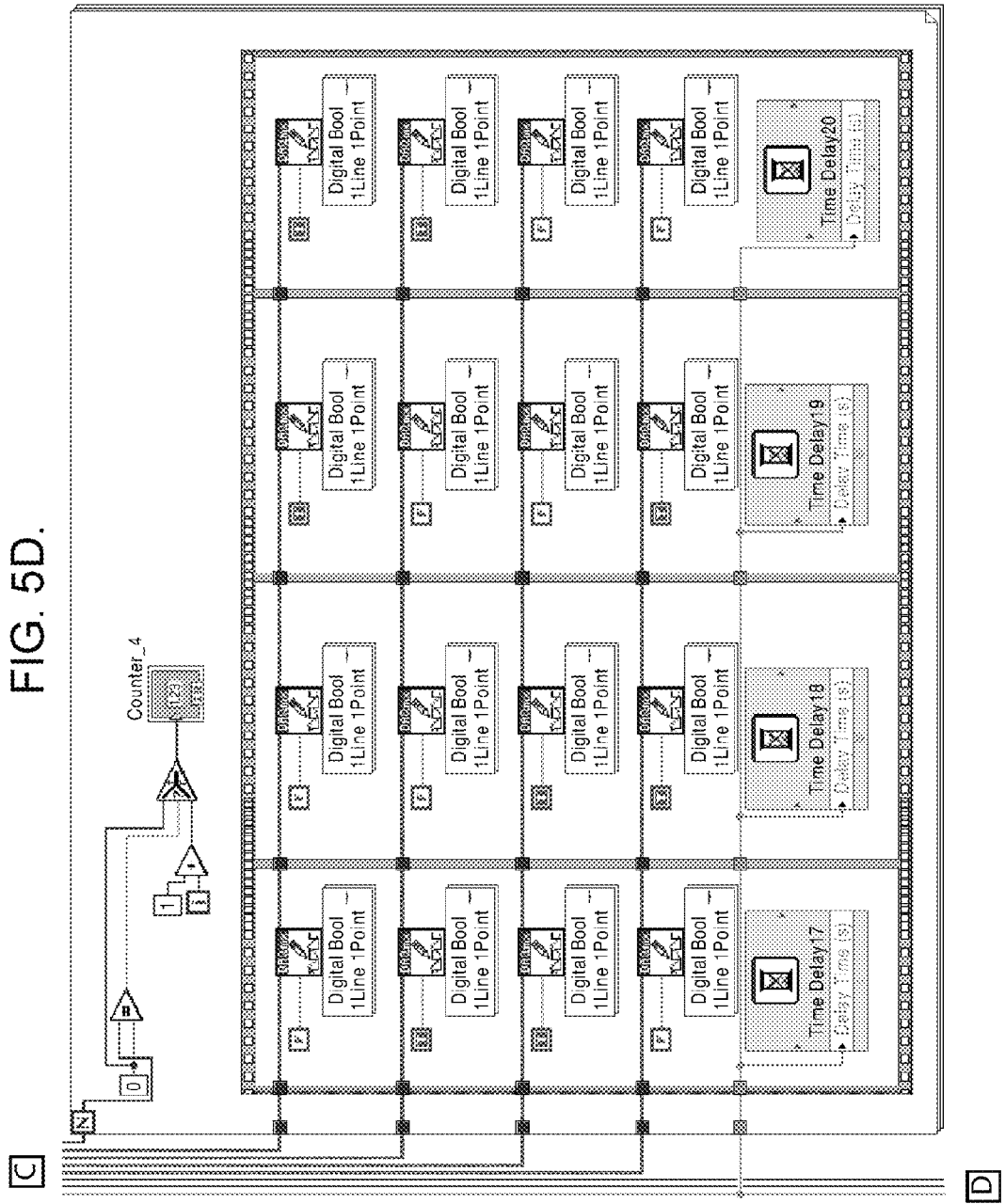
Figure 5E:
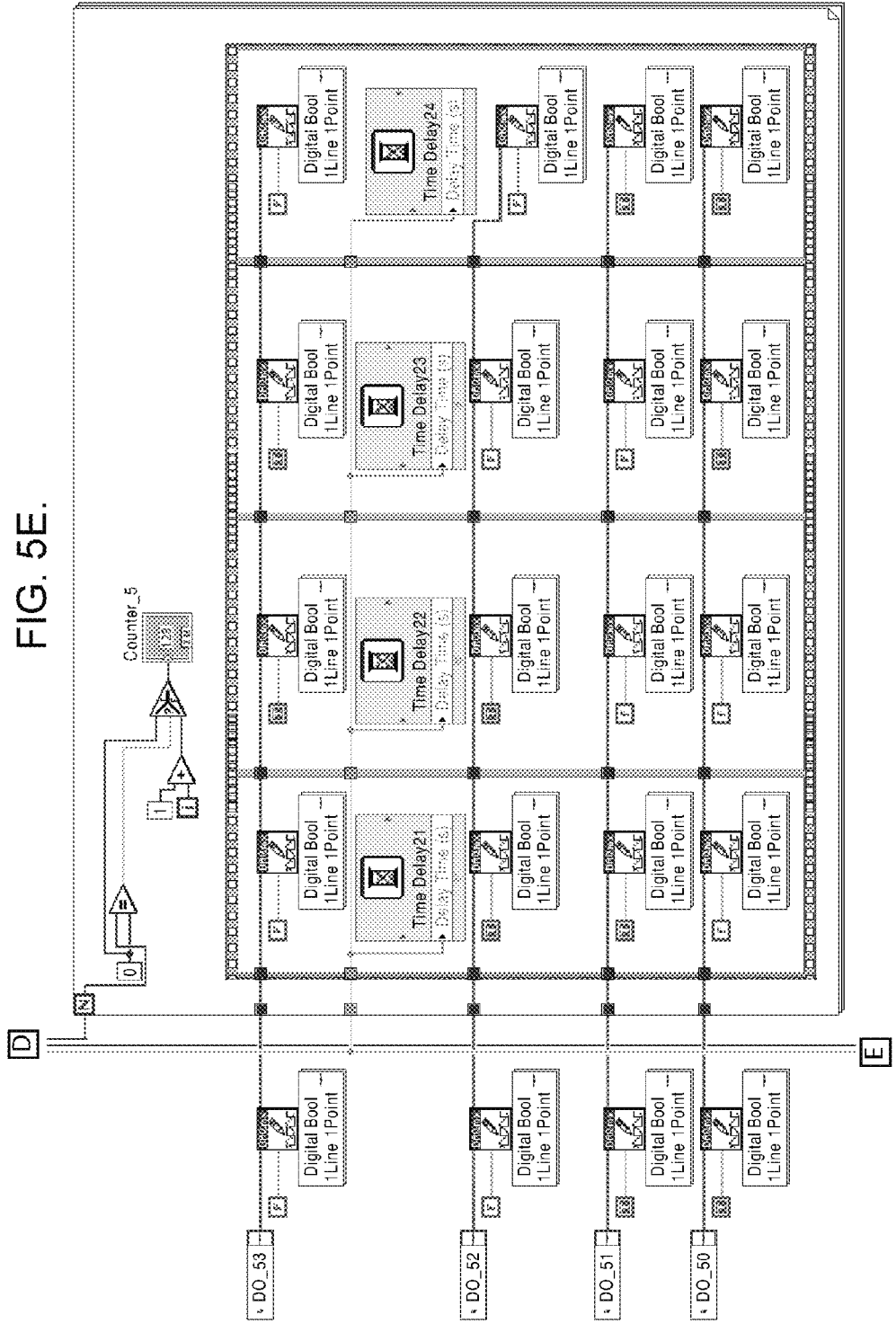
Figure 5F:
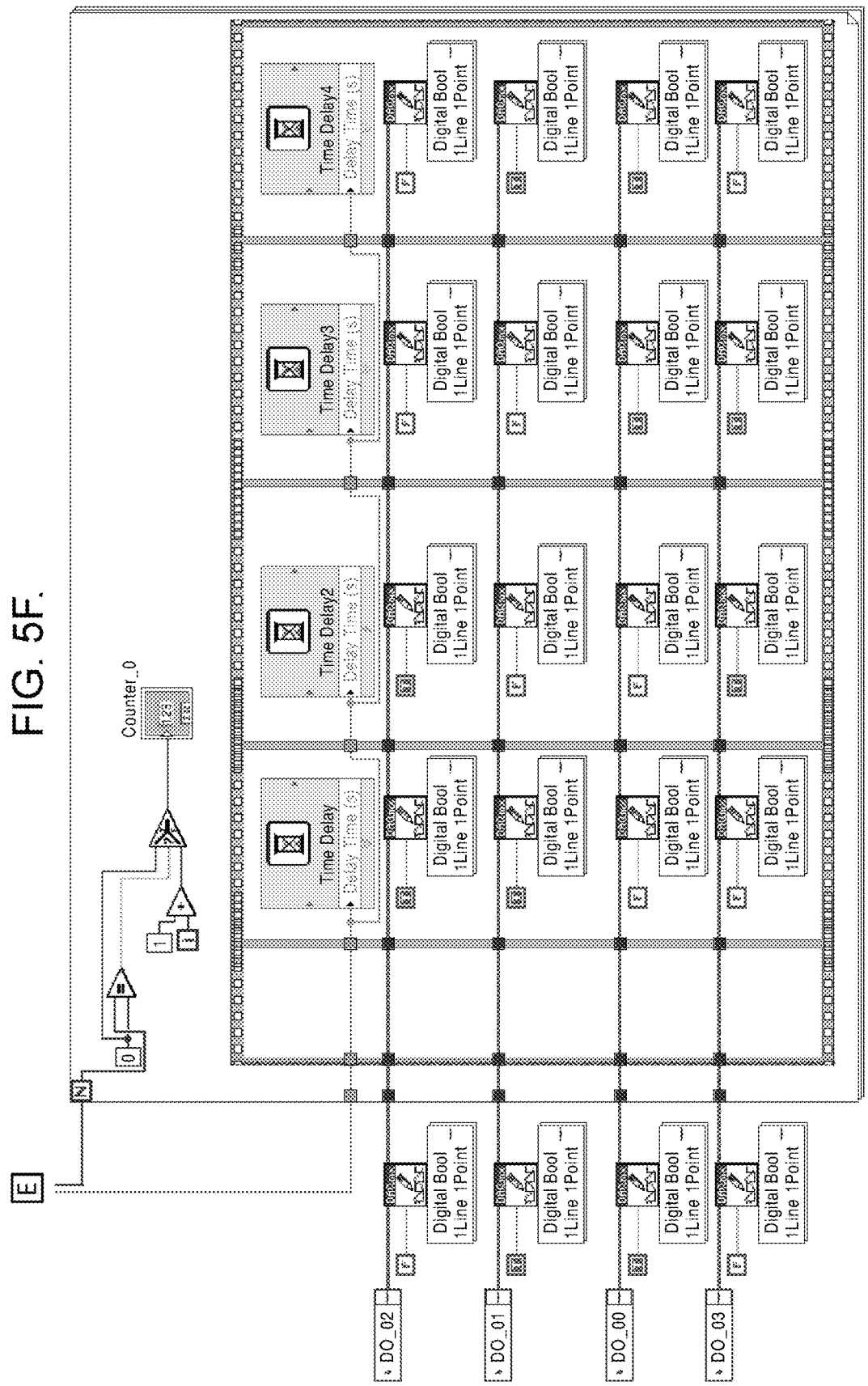

If the step is a "sample loading" step, the code asks the user to inject the sample in the elution column, using the front port of the 3-way diaphragm valve located below the mixing chamber (FIGS. 3A and 3B). The user clicks "Ok" when the injection is completed, which triggers the next elution step.

FIG. 4 depicts actuation of the (14+3) valves of the manifolds placed downstream from the elution column. Each successive frame on FIG. 4 corresponds to the condition of activation of a given port on one of the manifolds. For example, such ports herein are designated as MF0, MF1, MF2, etc.

FIG. 5 depicts status conditions and activation steps of the pumps status of the system. For example, a suitable program such as that depicted in FIG. 3, will drive a six step process as follows:

STEP A Runs a sub program, depicted in FIG. 6, called 1 (Robo_cal) (Note: Subprogram 1 Robo_cal reads and evaluates whether the input file is valid, and calculates the number of pump strokes required in order to obtain the desired total mixture volume quantity and concentration of each solvent.)

1. Open input file: The user is prompted to choose the input file that contains the following information:
 (i) Reservoir information, includes the types of reagent in each reservoir, the unit of concentration (molarity or volume %), and dispense volume/stroke of each pump
 (ii) Elution program, includes whether the step is "load" or not, total quantity (e.g., volume) of mixture to be prepared, desired concentration of each reagent in the mixture, mixing time and ID number of the manifold to which elution is directed. This software calculates the cumulative elution quantity, such as volume.

2. For each reservoir and elution steps, the volume of solution required to achieve the desired final mixture are calculated as follows
 (i) The program evaluates whether the concentration unit is in "%" or "mol/l"
 (ii) The program calculates the volume of the solution to be dispensed from each reservoir as follows:
 (a) "%" unit of concentration: Desired concentration (%)/100*Total volume (ml)
 (b) "mol/l" unit of concentration: Desired concentration (mol/l)/Reservoir concentration (mol/l)*Total volume (ml). An input concentration of "Balance" is allowed for one reagent per elution step. When the total volume of a particular reagent required to achieve the desired molarity is less than the total volume desired, the reagent with "Balance" (often water for mixtures involving acid) input will be added to achieve the desired total volume.

3. The subprogram 1 evaluates whether the input parameters of each elution step are valid. If the step title is "Load", the input parameters do not matter and the step is valid and will be a loading step. If the step title in not "load", then, preferably, the following conditions are satisfied:
 (i) There cannot be negative input of concentration;
 (ii) There can be at most one "Balance" per elution step;
 (iii) Total volume of reagents calculated (excluding "Balance") cannot exceed the total desired volume;
 (iv) Total volume of reagents calculated matches that of input within 0.1%
 (v) Total input volume of reagents does not exceed the mixing chamber capacity (10 ml)
 (vi) Manifold name corresponds to existing one. In the embodiment of the system using the X-Y stage, a stage position is expected instead of a manifold name.

These conditions need to be satisfied for all elution steps. This step will then generates an array of TF booleans indicating whether each elution step has valid input parameters and a boolean that indicates whether overall input parameters are valid and thus that the elution sequence is performable.

4. For each elution step, the subprogram 1 calculates the numbers of pump strokes to perform for each reservoir based on the dispensing volume per stroke of each pump and the total volume to dispense.

5. The subprogram 1 calculates the expected concentrations of each reagent based on the number of pump strokes calculated in Step 4.

Figure 6A:
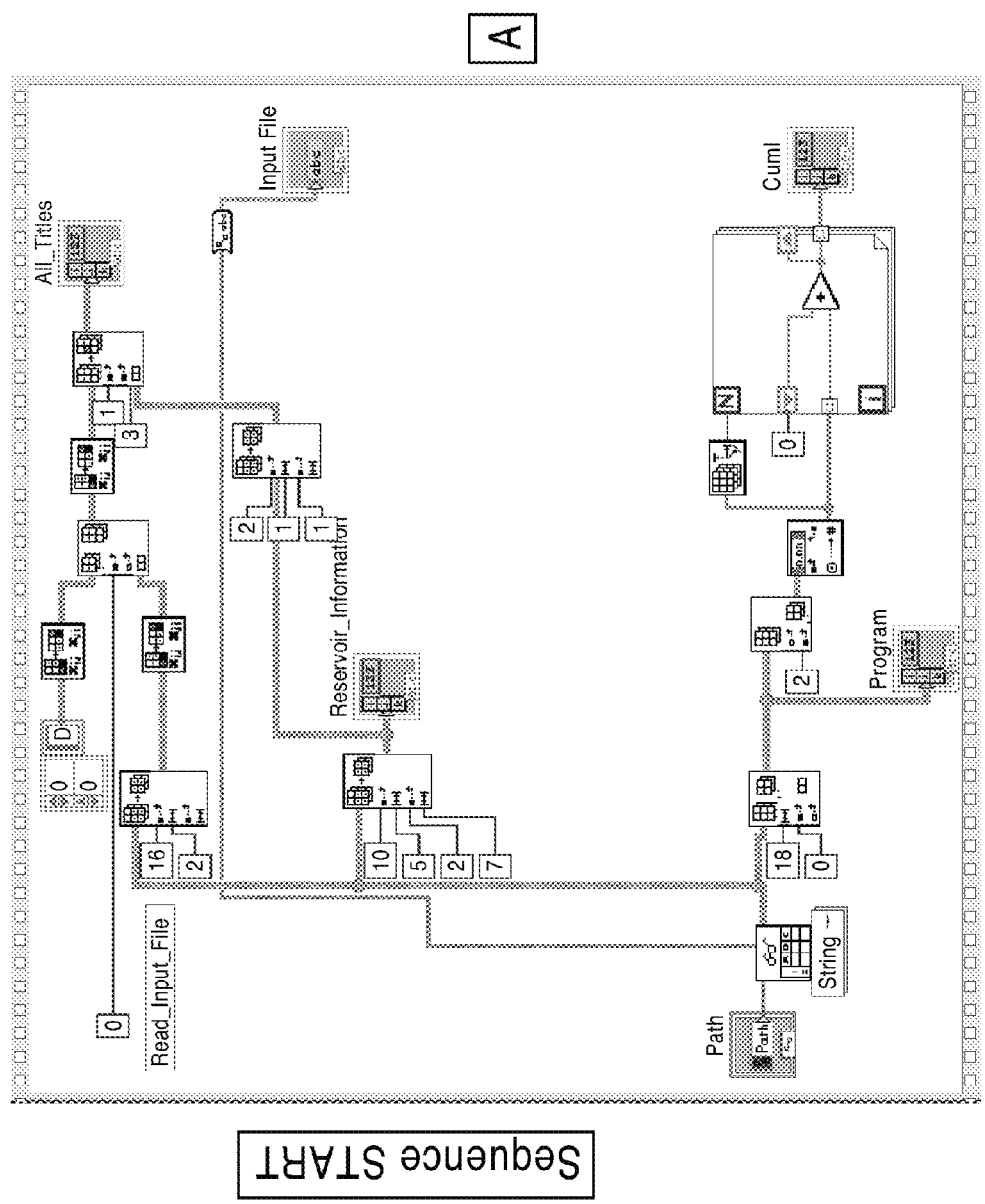
FIG. 6A is software code reading the input file provided by the user, in accordance with features of the present invention.
Figure 6B:
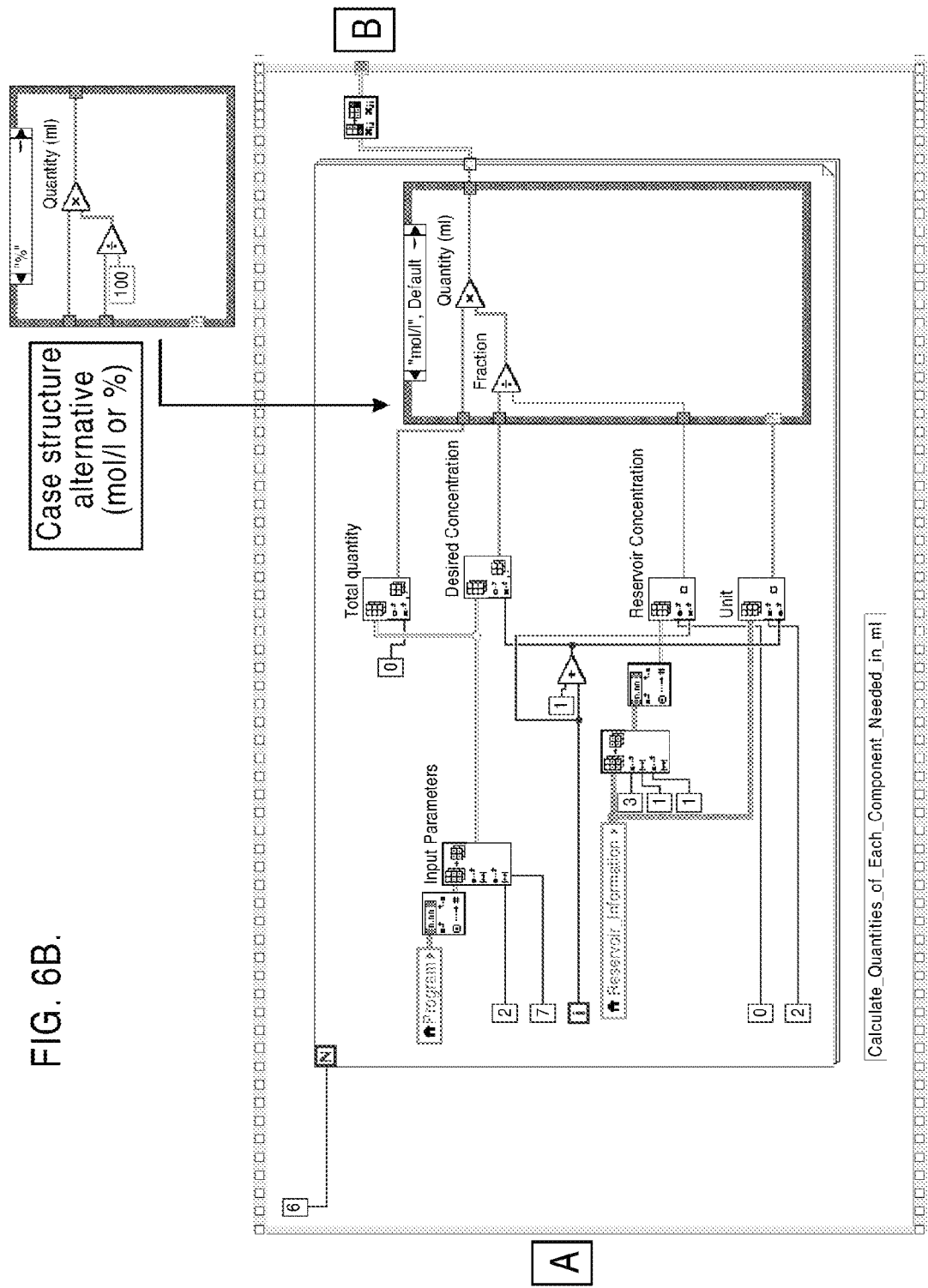
FIG. 6B is software code determining the quantities of each reagent needed to achieve the elution sequence as written on the input file, in accordance with features of the present invention.
Figure 6C:
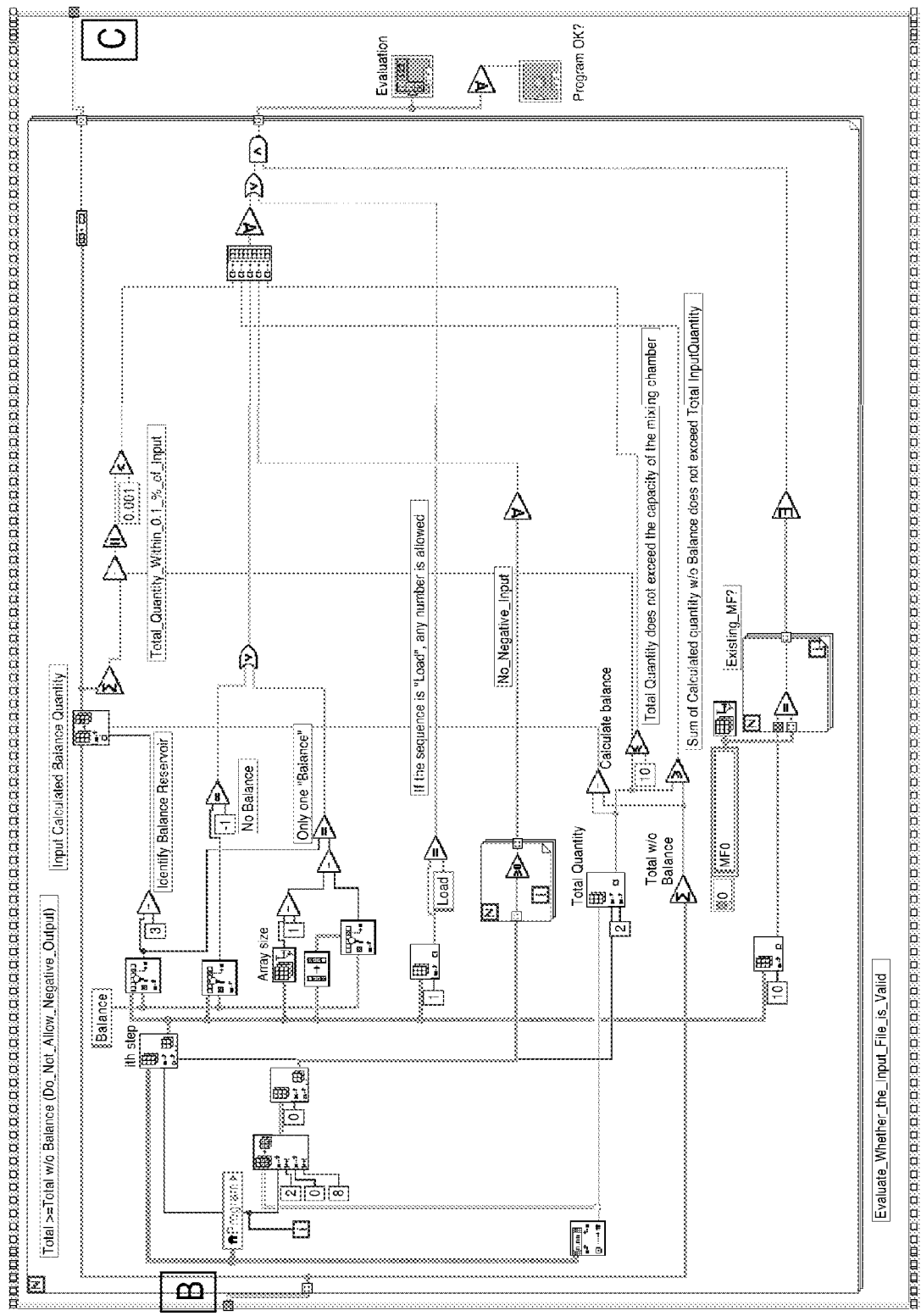
FIG. 6C is software code to evaluate the validity of input file data, in accordance with features of the present invention.
Figure 6D:
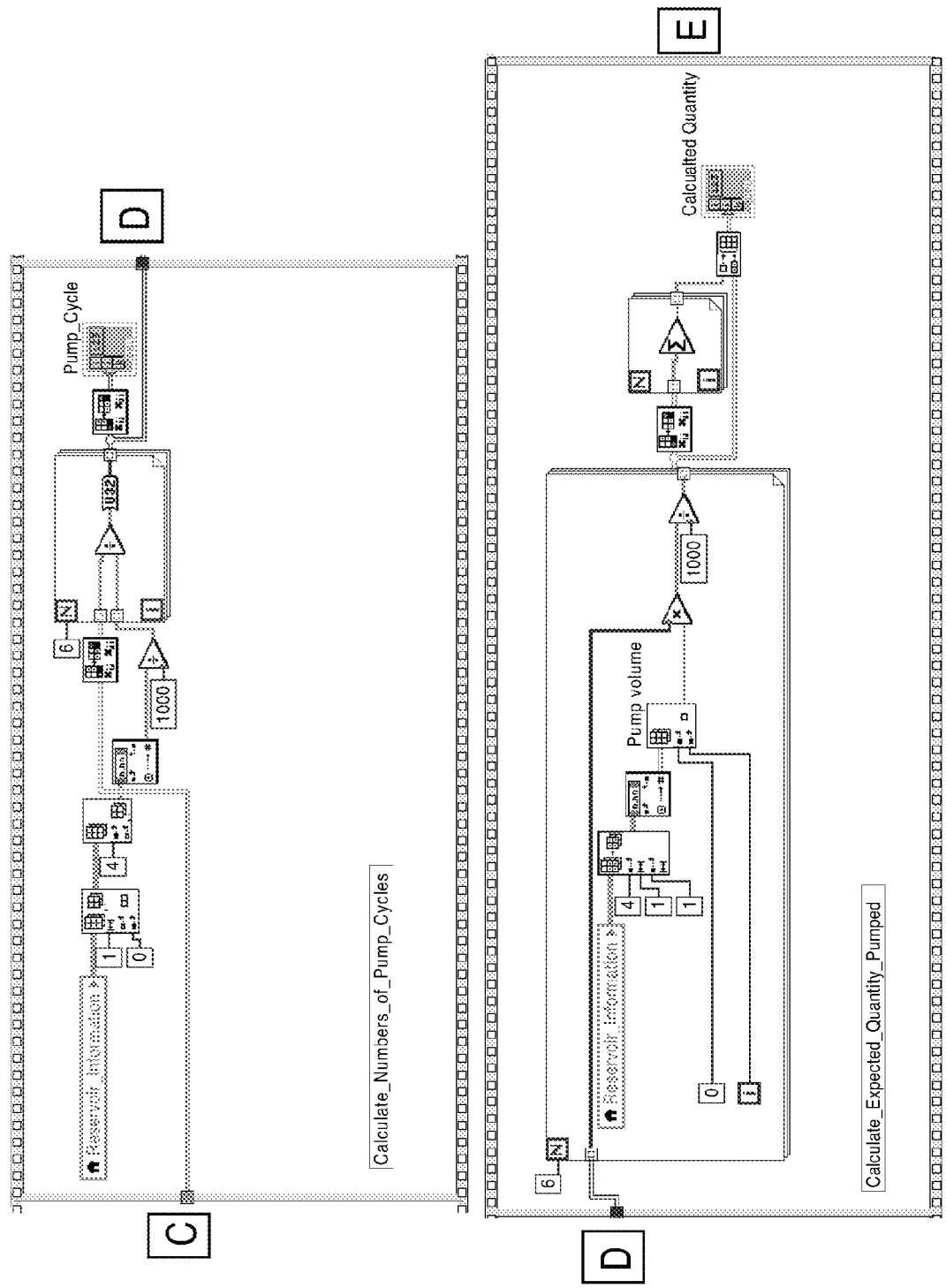
FIG. 6D is software code to calculate the number pump strokes required by the input file, as well as the expected pump volume of each reagent, in accordance with features of the present invention.
Figure 6E:
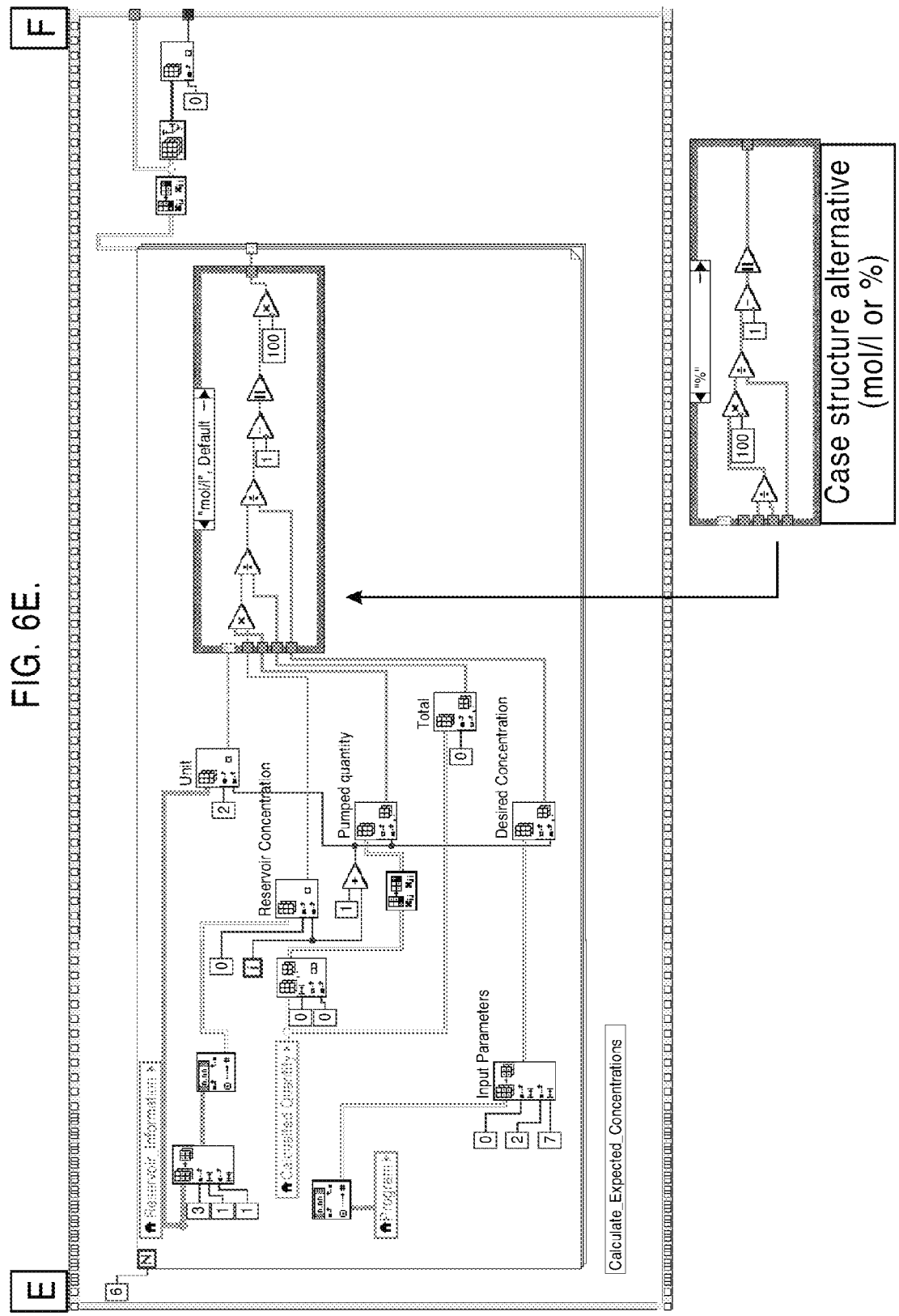
FIG. 6E is software code to calculate the concentrations of each reagent, in accordance with features of the present invention.
Figure 6F:
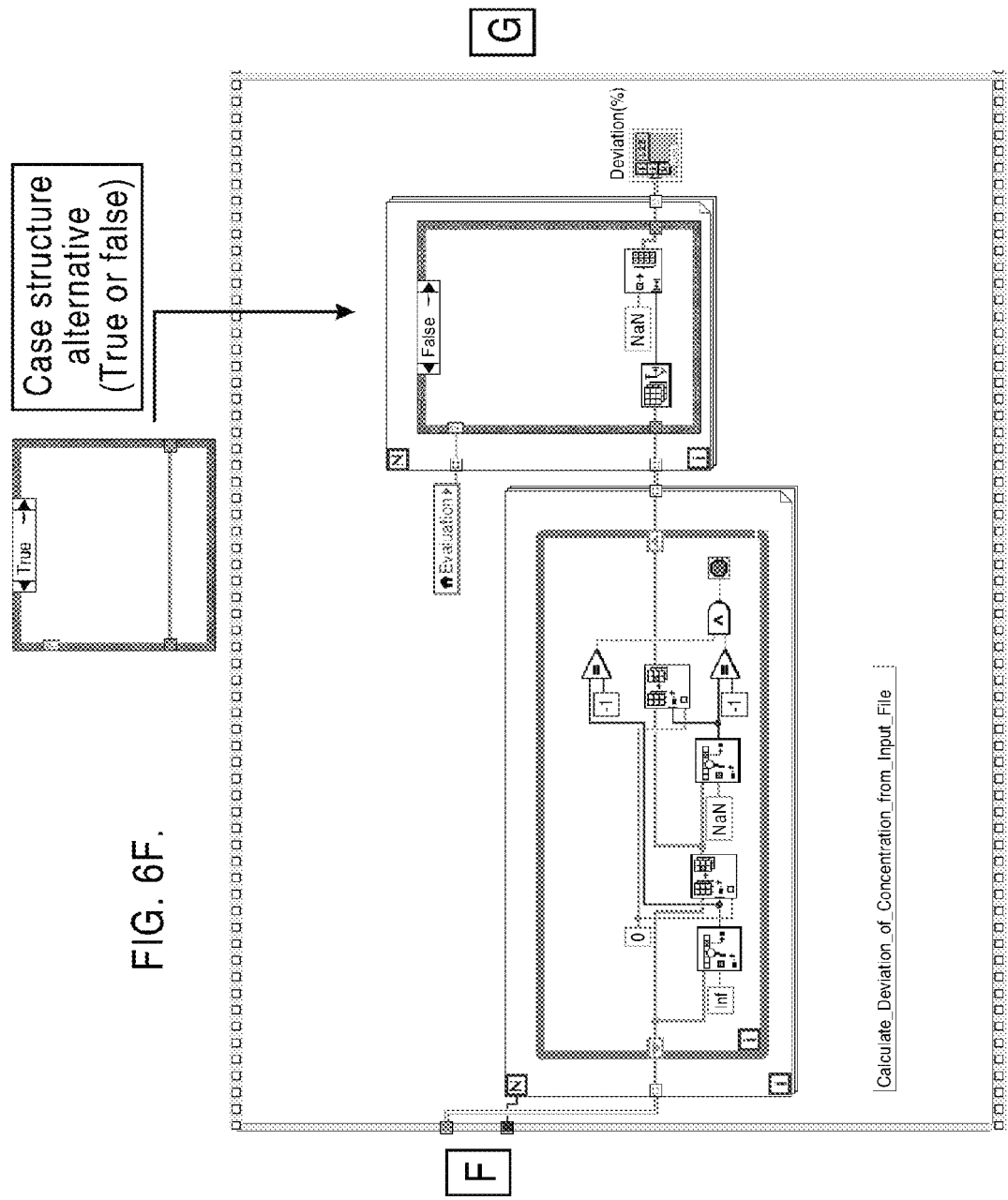
FIG. 6F depicts software schematic for calculating the deviation of reagent concentrations, in accordance with features of the present invention.
Figure 6G:
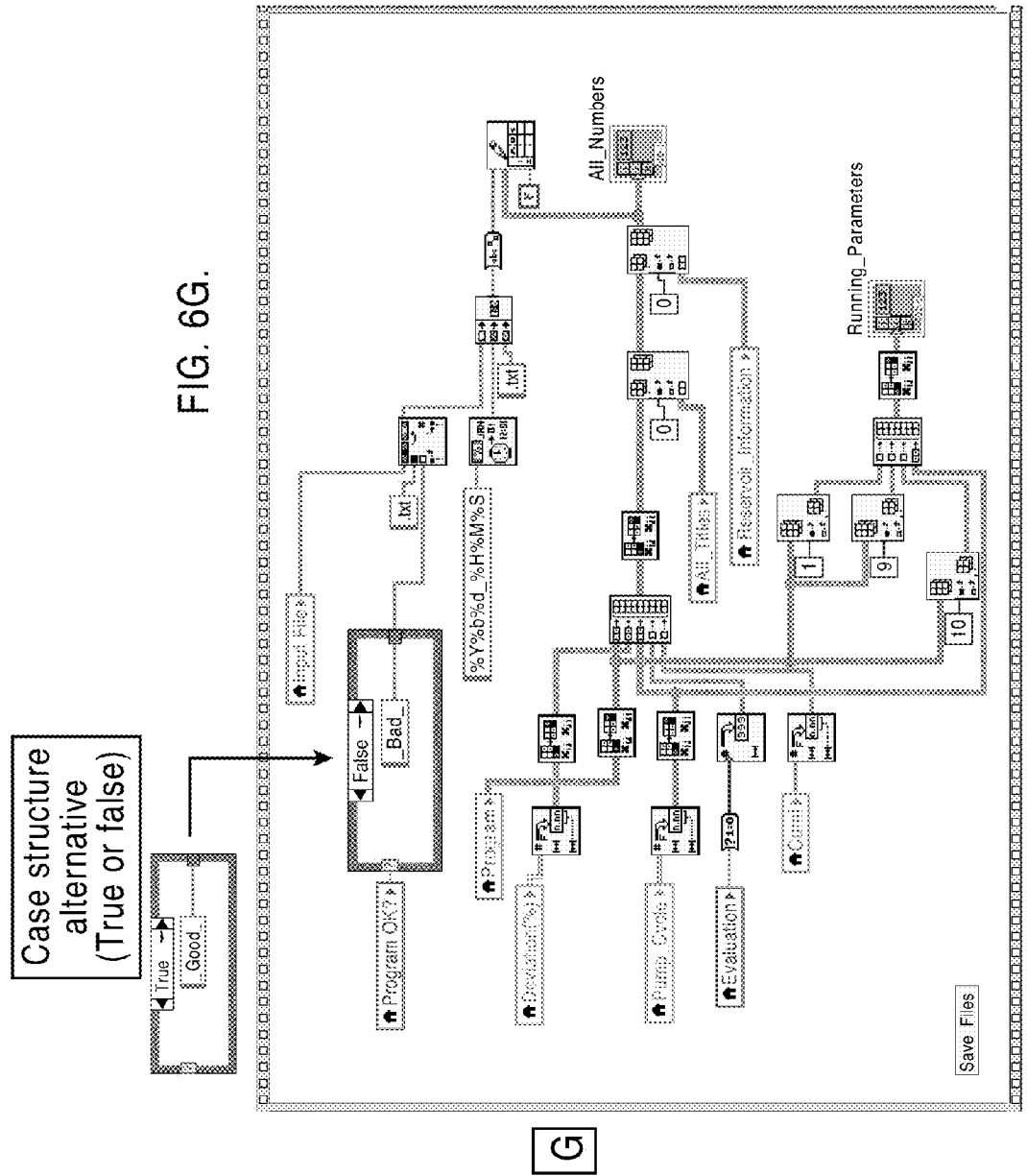
FIG. 6G depicts software schematic for export of a text file containing the input parameters and the values calculated by the code, in accordance with features of the present invention.

6. The subprogram 1 calculates the deviation of the expected concentration of each reagent from that of the input (desired concentrations), and record the deviation (in %) if the input parameters of the step are valid. (If not, it is recorded as "NaN"). FIG. 6F is software code to calculate the percent difference between the reagent concentration provided by the user in the input file and the closest reagent concentration achievable by the system given the finite pump stroke volume and reagents available. FIG. 6G exports a text file containing the input parameters and the values calculated by the code (i.e., number of pump strokes, elution volumes, concentrations of the prepared mixtures, and deviation from the set values entered by the user);

7. The subprogram 1 saves the input parameters, the cumulative elution volume from step 1, the evaluation results as boolean (from step 3), the number of pump strokes for each reservoir and each elution step (from step 4), and the expected concentration compared to the input (from step 6). The file will have a name of the type "input file+ whether the full sequence of elution steps has valid parameters or not (Good or Bad)+ Time+.txt and will be saved in the same directory as the input file.

STEP B: Displays the input and calculated parameters from the subprogram 1. If the input parameters are invalid, the program terminates and a message is displayed. Boolean indicators are available to show the problematic elution step(s). If the input parameters are valid, it asks whether the user would like to proceed. If the user doesn't want to proceed, the program terminates.

STEP C: Extract information from the subprogram 1 (the step type, the numbers of pump strokes, the mixing time and the manifold port involved for each elution step), and reading of liquid level sensor is taken every seconds (displayed as boolean indicator). An emergency "STOP" button is also checked every seconds and the elution program is aborted when pressed.

STEP D: The following series of procedures are run for each elution step. The number of completed elution steps is counted and the current step number is displayed. Each elution step is marked with a Boolean.

1. All pump solenoids off.
2. Evaluate whether the sequence step is "load". If TRUE, the code asks the user to "Remove the cap and locate the sample injection syringe" in the third port of the 3-way diaphragm valve located below the mixing chamber. Once ready for sample injection the user clicks "Ok". This triggers the opening of the valve connecting the syringe to the elution column. A new message is displayed which asks the user to "Load your sample. Click OK when you complete loading". This last click of the user closes the valve connecting the syringe to the elution column and triggers the next elution step. Note that in the embodiment of the invention using the sample injection loop and X-Y-stage, the software is modified to control these two components.

If FALSE, (i) the code reads the number of pump strokes to perform, and runs the pump for the required number of strokes. The approximate number of current strokes is counted and displayed, as depicted in FIGS. 3C and 3D.

(ii) The valve actuating the stirring bar is opened for the amount of time specified in the input file. The actual mixing time is also displayed.

(iii) The stirring bar is deactivated and the valve between the elution column and the mixing chamber is opened. The chamber is then pressurized and the manifold valve is opened, allowing the mixture to be pushed through the elution column and collected into one of the collecting vials at the bottom of the column. During the elution, the elution boolean is shown active and the time of elution is displayed and recorded.

(iv) Once the liquid level reaches below the level sensor at the bottom of the mixing chamber (i.e., the mixing chamber is empty), the valve between the elution column and the mixing chamber is closed, the chamber is vented, the tubing and components downstream of the columns are purged of any eluted liquid (this step not shown in the appended code), after what the manifold valve at the bottom of the elution column is closed and the next elution step starts.

STEP E: After all elution steps have been performed, solenoids for all valves and pumps are turned off.

STEP F: The message "Program complete" is displayed and a graphic showing the elution time as a function of the cumulative eluted volume is plotted.

EXAMPLE 1

The inventors tested the effectiveness of the invented system on two diverse column techniques that are particularly challenging and exemplify the unprecedented capability of the PF-HPLC system. An embodiment of the first application involved the separation of Ni from Mg, for example, for high precision Ni isotopic studies and for studies interested in the abundance of the extinct 60Fe radionuclide. In the past, one of the required column steps had to be repeated up to 5 times to ensure adequate separation of trace Ni from Mg. This column step involved using a mixture of acetone and HCl on a 40 cm long column, in a procedure that would take ~14 hours per pass (up to 70 hours total for 5 passes). Since acetone evaporates rather quickly, preferably, the column reagents are freshly remixed on a regular basis (e.g., every hour).

The afore described PF-HPLC system greatly simplifies and improves upon the old technique. In a single, automated pass on an 80 cm long column, the achieved improved separation of Ni from Mg, with a much improved time frame. A quantitative way to characterize the separation efficiency of a chromatographic set-up is to calculate the resolution of two successive elution peaks. Resolution is defined as $$R = \frac{(V_2 - V_1)}{2\sigma_2 + 2\sigma_1}$$

with V the eluate volume at the peak maximum, $2\sigma$ the peak width at a height $e^{-1/2}$ times the peak height, and the subscripts refer to the successive peaks. The separation resolution of Ni—Mg with the traditional set-up is 1.15 against 1.82 with the PF-HPLC, which is a 58% improvement. The time frame improved from 5×14 h with the traditional set-up to 1×10 h with the PF-HPLC, which is 86% less time.

EXAMPLE 2

The second application the inventors tested was the separation of the individual rare earth elements from each other. A myriad of uses are envisioned for this feature. For example, the isotopic composition of the multi-isotopic REE (La, Ce, Nd, Sm, Eu, Gd, Dy, Er, Yb and Lu) may hold important information about nucleosynthetic processes, neutron capture and cosmic-ray exposure effects on meteorites, and mass fractionation effects. The ability to separate and analyze the isotopic composition of all of these elements from a single chemical digestion could represent a big step forward in our understanding of these processes. For this application, the inventors also developed a Mathematica code that uses experimentally determined partition coefficients to simulate an elution curve.

Overall, the inventors achieved surprising and unexpectedly high separation efficiencies of the multi-isotopic REE from each other, thereby demonstrating the effectiveness of the PF-HPLC system. To the best of the inventors' knowledge, the best average resolution for all REEs found in the literature is 1.73 and was achieved by Campbell 1973 in a stainless steel system. Using the PF-HPLC system and the same chromatographic resin and eluent as Campbell the inventors achieved an average resolution of 3.48 for REEs. This is a resolution improvement of 100 percent.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting, but are instead exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the terms "comprising" and "wherein." Moreover, in the following claims, the terms "first," "second," and "third," are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

The embodiment of the invention in which an exclusive property or privilege is claimed is defined as follows:

1. A high-performance liquid chromatography apparatus, said apparatus comprising:
   a flow path comprising:
      a plurality of reagent reservoirs, wherein each of the plurality of reagent reservoirs are in contact with a plurality of fluoropolymer coils, each fluoropolymer coil containing a heat carrying fluid, and wherein each of the plurality of reagent reservoirs is charged with a liquid-phase reagent;
      a plurality of metering pumps in fluid communication with and downstream from the plurality of reagent reservoirs that transfer the liquid-phase reagent from the plurality of reagent reservoirs to the mixing chamber;
      a mixing chamber in fluid communication with and downstream from the plurality of reagent reservoirs, wherein the liquid phase reagents are combined to form a reagent mixture, and wherein the mixing chamber is in contact with at least one of said fluoropolymer coils, wherein the mixing chamber is in computer controlled communication with a pressurized fluid;
      a sample injector in fluid communication with and downstream from the mixing chamber;
      a modular elution column in fluid communication with and downstream from the sample injector, wherein the modular elution column is surrounded by and in thermal contact with a fluid jacket containing the heat carrying fluid, and wherein a stream of eluent flows from a downstream end of the modular elution column;
      an automated fraction collector configured to collect a plurality of portions of the stream of eluent in a plurality of different receptacles wherein the pump, sample injector, and automated fraction collector comprise moving components, and wherein said moving components are pneumatically actuated; and
      a return line with a pump to automatically reload a desired portion of the stream of eluent onto the modular elution column, wherein the entire flow path is fabricated out of a material consisting of a fluoropolymer.

2. The apparatus of claim 1, further comprising a programmable system, wherein the programmable system controls introduction of the liquid-phase reagents, pumping and mixing of the liquid-phase reagents in the mixing chamber to achieve a desired concentration, elution of the reagent mixture through the modular elution column, and distribution of the plurality of portions of the stream of effluent in the plurality of different receptacles.

3. The apparatus of claim 1 further comprising a circulation path comprising a closed loop interconnecting the fluid jacket, the fluoropolymer coils, and a fluid circulator configured to bring the heat carrying fluid to a specific temperature and circulate the heat carrying fluid through the circulation path.

4. The apparatus of claim 1 wherein the fluoropolymer coils and fluid jacket form a closed system.

5. The apparatus of claim 1 wherein the temperature of the high-performance liquid chromatography system can be controlled and maintained from $-55°$ C. up to approximately $200°$ C.

6. The apparatus as recited in claim 1 wherein the modular elution column is pressurized by the pressurized fluid.

7. The apparatus as recited in claim 6 wherein the pressurized fluid is a gas selected from the group consisting of air, nitrogen, argon, helium, and combinations thereof.

8. The apparatus as recited in claim 1 wherein the heat carrying fluid is a liquid selected from the group consisting of water, oil, nonaqueous fluids having boiling points higher than water, and combinations thereof.

9. The apparatus of claim 1 wherein the automated fraction collector comprises a manifold mounted on a platform that can be moved up and down on two rails and the plurality of different receptacles are mounted on a second platform that can move up and down relative to the manifold to allow for flexibility in length of elution column and height of elution receptacles.

10. The apparatus of claim 1 wherein the automated fraction collector comprises an X-Y pneumatic moving stage with a plurality of predetermined positions mounted on a platform that can be moved up and down to allow for flexibility in length of elution column and height of elution receptacles.

11. The apparatus of claim 1 wherein the sample injector comprises a sample injection loop comprising:

a housing defining a first fluid inlet and a first fluid outlet a first body concentrically arranged within said housing, said first body in rotatable communication with said housing;

a plurality of separate passageways integrally molded within said first body wherein each of said passageways has a first end that terminates in a fluid inlet and further wherein each of said passageways has a second end that terminates in a fluid outlet; and a sample storage conduit having a first end in fluid communication with the fluid outlet of one of said passageways and a second end in fluid communication with the fluid inlet of another of said passageways.

12. The apparatus of claim 11 wherein the sample injection loop is comprised substantially of fluoropolymer.

13. The apparatus of claim 1 wherein the sample injector comprises a pneumatically-actuated valve in fluid communication with and downstream from the mixing chamber.

14. The apparatus of claim 1 wherein the flow path tolerates pressures up to 80 psi.

15. The apparatus of claim 1 further comprising a corrosion resistant electronics box having an interior containing a plurality of solenoid valves that actuate the moving parts of the flow path.

16. The apparatus of claim 15 wherein the interior of the electronics box is not in fluid communication with the flow path.

* * * * *